United States Patent
Bosua

(10) Patent No.: US 11,193,923 B2
(45) Date of Patent: Dec. 7, 2021

(54) DETECTION OF AN ANALYTE USING MULTIPLE ELEMENTS THAT CAN TRANSMIT OR RECEIVE

(71) Applicant: Know Labs, Inc., Seattle, WA (US)

(72) Inventor: Phillip Bosua, Seattle, WA (US)

(73) Assignee: KNOW LABS, INC., Seattle, WA (US)

( * ) Notice: Subject to any disclaimer, the term of this patent is extended or adjusted under 35 U.S.C. 154(b) by 0 days.

(21) Appl. No.: 17/164,086

(22) Filed: Feb. 1, 2021

(65) Prior Publication Data

US 2021/0247379 A1    Aug. 12, 2021

Related U.S. Application Data

(60) Provisional application No. 62/971,048, filed on Feb. 6, 2020.

(51) Int. Cl.
*G01N 33/487* (2006.01)
*G01N 33/98* (2006.01)
*G01N 33/569* (2006.01)

(52) U.S. Cl.
CPC .. *G01N 33/48785* (2013.01); *G01N 33/48707* (2013.01); *G01N 33/56972* (2013.01); *G01N 33/98* (2013.01)

(58) Field of Classification Search
None
See application file for complete search history.

(56) References Cited

U.S. PATENT DOCUMENTS 4,202,000 A    5/1980 Carballes
8,223,021 B2   7/2012 Goodnow et al.
(Continued)

FOREIGN PATENT DOCUMENTS

JP    2012125382    7/2012
JP    2014147637    8/2014
(Continued)

OTHER PUBLICATIONS

Hanna, J. et al., "Noninvasive, wearable, and tunable electromagnetic multisensing system for continuous glucose monitoring, mimicking vasculature anatomy," Science Advances, 6, eaba5320,2020 (11 pages).
(Continued)

*Primary Examiner* — Matthew D Krcha
(74) *Attorney, Agent, or Firm* — Hamre, Schumann, Mueller & Larson, P.C.

(57) ABSTRACT

A method of detection of an analyte includes using a detector array having at least two detector elements that can emit electromagnetic waves, and selectively connecting a transmit circuit to any one or more of the at least two detector elements of the detector array. At least one transmit signal is generated using the transmit circuit, where the at least one transmit signal is in a radio or microwave frequency or visible range of the electromagnetic spectrum. The at least one transmit signal is transmitted into a target containing at least one analyte of interest using the one or more of the at least two detector elements connected to the transmit circuit. A receive circuit is selectively connected to a different one or more of the at least two detector elements of the detector array, and the receive circuit and the different one or more of the at least two detector elements of the detector array are used to detect a response resulting from transmission of the at least one transmit signal into the target containing the at least one analyte of interest.

24 Claims, 20 Drawing Sheets

(56) References Cited

U.S. PATENT DOCUMENTS

| | | | |
|---|---|---|---|
| 8,882,670 B2* | 11/2014 | Hancock | A61B 5/14532 600/309 |
| 9,198,607 B2 | 12/2015 | Fischer | |
| 9,864,024 B2 | 1/2018 | Vester | |
| 10,149,629 B2 | 12/2018 | Szczepaniak et al. | |
| 10,478,101 B1 | 11/2019 | Cespedes et al. | |
| 10,548,503 B2 | 2/2020 | Bosua | |
| 2003/0036713 A1 | 2/2003 | Bouton et al. | |
| 2004/0065158 A1 | 4/2004 | Schrepfer et al. | |
| 2004/0127777 A1 | 7/2004 | Ruchti et al. | |
| 2004/0133086 A1 | 7/2004 | Ciurczak et al. | |
| 2009/0275814 A1 | 11/2009 | Watanabe et al. | |
| 2010/0041969 A1 | 2/2010 | Beise | |
| 2011/0028814 A1 | 2/2011 | Petersen et al. | |
| 2013/0096396 A1 | 4/2013 | Riedel | |
| 2014/0213870 A1 | 7/2014 | Hsu et al. | |
| 2016/0051171 A1 | 2/2016 | Pikov et al. | |
| 2016/0361002 A1 | 12/2016 | Palikaras et al. | |
| 2017/0095667 A1 | 4/2017 | Yakovlev et al. | |
| 2018/0028824 A1 | 2/2018 | Pivonka et al. | |
| 2018/0132766 A1 | 5/2018 | Lee et al. | |
| 2019/0008422 A1 | 1/2019 | Leath et al. | |
| 2019/0053741 A1 | 2/2019 | Chaudhry | |
| 2019/0104939 A1 | 4/2019 | Costantine et al. | |
| 2019/0357800 A1* | 11/2019 | Bosua | A61B 5/0507 |
| 2019/0374135 A1 | 12/2019 | Poeze et al. | |
| 2019/0388000 A1 | 12/2019 | Costantine et al. | |
| 2020/0057163 A1 | 2/2020 | Bromberg | |
| 2020/0146584 A1 | 5/2020 | Bosua | |
| 2020/0187791 A1 | 6/2020 | Leabman | |
| 2020/0187792 A1 | 6/2020 | Leabman | |
| 2020/0187793 A1* | 6/2020 | Leabman | A61B 5/7257 |
| 2020/0187812 A1 | 6/2020 | Leabman | |
| 2020/0187813 A1 | 6/2020 | Leabman | |
| 2020/0187814 A1 | 6/2020 | Leabman | |
| 2020/0187815 A1 | 6/2020 | Leabman | |
| 2020/0187816 A1 | 6/2020 | Leabman | |
| 2020/0187817 A1 | 6/2020 | Leabman | |
| 2020/0187818 A1 | 6/2020 | Leabman | |
| 2020/0187819 A1 | 6/2020 | Leabman | |
| 2020/0187820 A1 | 6/2020 | Leabman | |
| 2020/0187836 A1 | 6/2020 | Leabman | |
| 2020/0187837 A1 | 6/2020 | Leabman | |
| 2020/0187867 A1 | 6/2020 | Leabman | |
| 2020/0191909 A1 | 6/2020 | Leabman | |
| 2020/0191932 A1 | 6/2020 | Leabman | |
| 2020/0191933 A1 | 6/2020 | Leabman | |
| 2020/0191944 A1 | 6/2020 | Leabman | |
| 2020/0191945 A1 | 6/2020 | Leabman | |
| 2020/0191947 A1 | 6/2020 | Leabman | |
| 2020/0192426 A1 | 6/2020 | Leabman | |
| 2020/0192427 A1 | 6/2020 | Leabman | |
| 2020/0192428 A1 | 6/2020 | Leabman | |
| 2020/0193326 A1 | 6/2020 | Leabman | |
| 2020/0195197 A1 | 6/2020 | Leabman | |
| 2020/0195293 A1 | 6/2020 | Leabman | |

FOREIGN PATENT DOCUMENTS

| | | |
|---|---|---|
| KR | 1020160081740 | 7/2016 |
| WO | 2017163245 | 9/2017 |
| WO | 2019071138 | 4/2019 |
| WO | 2019182638 | 9/2019 |
| WO | 2019217461 | 11/2019 |
| WO | 2020006077 | 1/2020 |
| WO | 2020037171 | 2/2020 |

OTHER PUBLICATIONS

"Contributes to longer healthy life expectancy with non-invasive vital acquisition sensor," Quantum Operation Co., Ltd., presentation found on Jan. 12, 2021 at https://oi.nttdata.com/program/forum/history/20191118/pdf/03_quantum-op.pdf (14 pages including English translation).

International Search Report and Written Opinion for PCT/US2019/031176, dated Aug. 23, 2019, 9 pages.

Qiang et al., "Quantitative detection of glucose level based on radiofrequency patch biosensor combined with volume-fixed structures," Biosensors and Bioelectronics 98:357-363, 2017.

Shaker, G. et al., "Non-Invasive Monitoring of Glucose Level Changes Utilizing a mm-Wave Radar System," IJMHCI, vol. 10, Issue 3 (2018): pp. 10-29.

Lien, J. et al., "Soli: Ubiquitous Gesture Sensing with Millimeter Wave Radar," ACM Trans. Graph., vol. 35, No. 4, Article 142, 19 pages (Jul. 2016).

Stojanovic, R. et al., "An optical sensing approach based on light emitting diodes," Journal of Physics: Conference Series 76 (2007), pp. 1-6.

Rossiter, J. et al., "A novel tactile sensor using a matrix of LEDs operating in both photoemitter and photodetector modes," Proc of 4th IEEE International Conference on Sensors (IEEE Sensors 2005), pp. 994-997.

U.S. Appl. No. 17/123,932, titled "Non-Invasive Analyte Sensor and System With Decoupled Transmit and Receive Antennas," filed Dec. 16, 2020 (49 pages).

U.S. Appl. No. 17/123,947, titled "Non-Invasive Detection of an Analyte Using Decoupled Transmit and Receive Antennas," filed Dec. 16, 2020 (46 pages).

U.S. Appl. No. 17/123,961, titled "Non-Invasive Analyte Sensor and System With Decoupled and Inefficient Transmit and Receive Antennas," filed Dec. 16, 2020 (48 pages).

U.S. Appl. No. 17/123,977, titled "Non-Invasive Detection of an Analyte Using Decoupled and Inefficient Transmit and Receive Antennas," filed Dec. 16, 2020 (47 pages).

U.S. Appl. No. 17/123,992, titled "Non-Invasive Analyte Sensor Device," filed Dec. 16, 2020 (47 pages).

U.S. Appl. No. 17/164,073, titled "Analyte Sensor and System With Multiple Detector Elements That Can Transmit or Receive," filed Feb. 1, 2021 (65 pages).

U.S. Appl. No. 17/164,103, titled "Detection of an Analyte Using Different Combinations of Detector Elements That Can Transmit or Receive," filed Feb. 1, 2021 (65 pages).

U.S. Appl. No. 17/171,279, titled "Non-Invasive Detection of an Analyte and Notification of Results," filed Feb. 9, 2021 (49 pages).

U.S. Appl. No. 17/171,281, titled "Non-Invasive Analyte Sensing and Notification System With Decoupled Transmit and Receive Antennas," filed Feb. 9, 2021 (49 pages).

U.S. Appl. No. 17/171,284, titled "Non-Invasive Analyte Sensing and Notification System With Decoupled and Inefficient Transmit and Receive Antennas," filed Feb. 9, 2021 (49 pages).

International Search Report and Written Opinion issued for International Patent Application No. PCT/IB2021/050805, dated May 4, 2021, 8 pages.

International Search Report and Written Opinion issued for International Patent Application No. PCT/IB2021/050838, dated May 6, 2021, 7 pages.

* cited by examiner

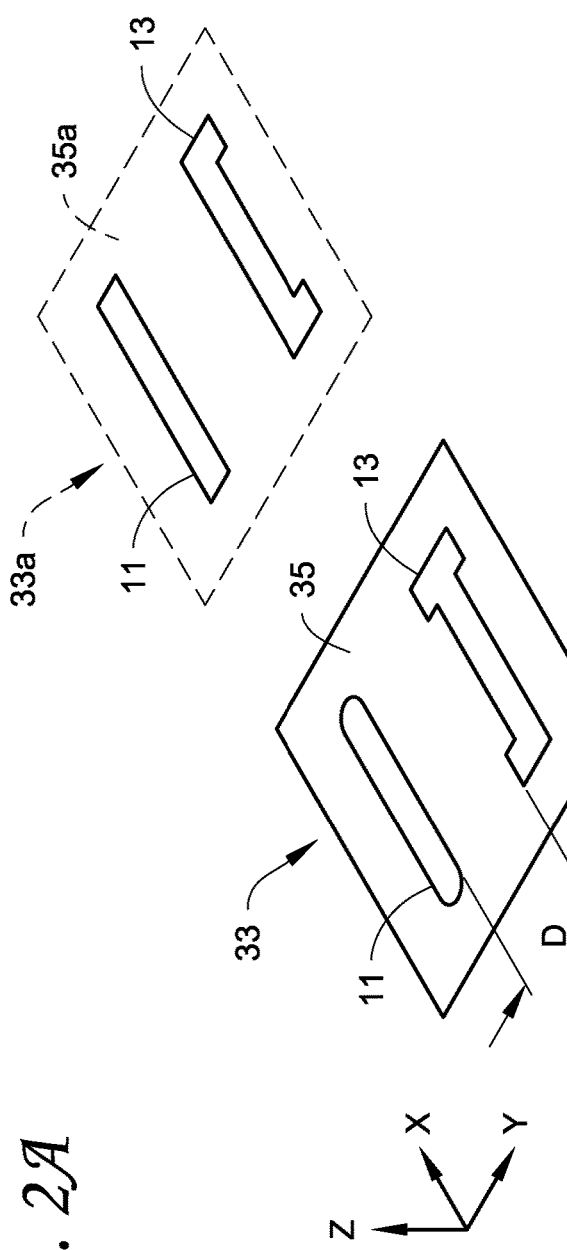
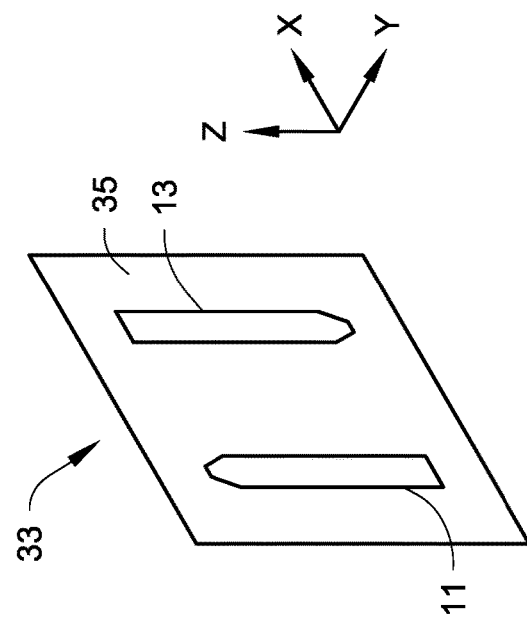
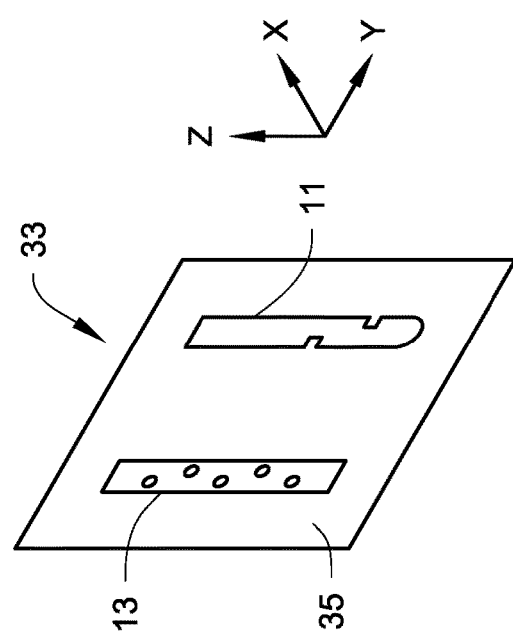
Fig. 2A
Fig. 2B
Fig. 2C

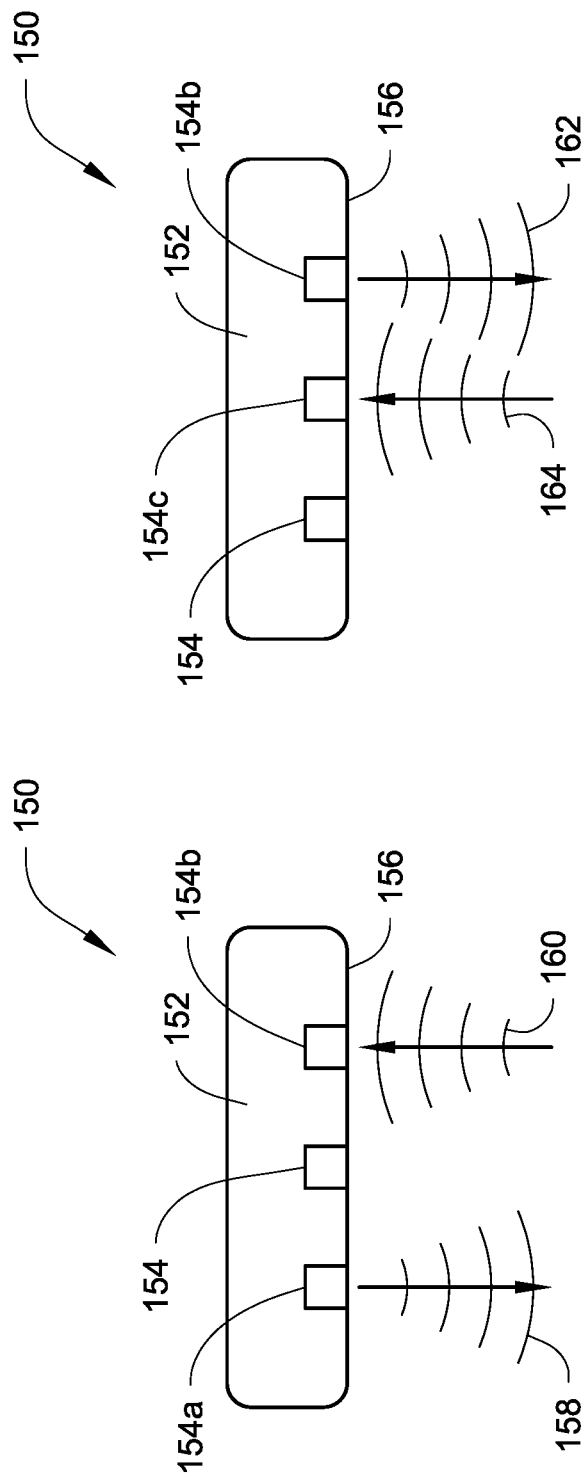

DETECTION OF AN ANALYTE USING MULTIPLE ELEMENTS THAT CAN TRANSMIT OR RECEIVE

FIELD

This disclosure relates generally to apparatus, systems and methods of detecting an analyte via spectroscopic techniques using an analyte sensor that includes at least two elements that can transmit and receive electromagnetic waves and that can be used as either a transmit detector element or as a receive detector element.

BACKGROUND

There is interest in being able to detect and/or measure an analyte within a target. One example is measuring glucose in biological tissue. In the example of measuring glucose in a patient, current analyte measurement methods are invasive in that they perform the measurement on a bodily fluid such as blood for fingerstick or laboratory-based tests, or on fluid that is drawn from the patient often using an invasive transcutaneous device. There are non-invasive methods that claim to be able to perform glucose measurements in biological tissues. However, many of the non-invasive methods generally suffer from: lack of specificity to the analyte of interest, such as glucose; interference from temperature fluctuations; interference from skin compounds (i.e. sweat) and pigments; and complexity of placement, i.e. the sensing device resides on multiple locations on the patient's body.

SUMMARY

This disclosure relates generally to apparatus, systems and methods of detecting an analyte via spectroscopic techniques using non-optical frequencies such as in the radio or microwave frequency bands of the electromagnetic spectrum or optical frequencies in the visible range of the electromagnetic spectrum. In an embodiment, the techniques described herein can be used for non-invasive detection of an analyte. In another embodiment, the techniques described herein can be used for in vitro detection of an analyte. An analyte sensor described herein includes a detector array having at least two detector elements that can transmit or receive electromagnetic waves. In one embodiment, the detector array can have at least three of the detector elements which can be antennas or light emitting elements such as light emitting diodes. Any one or more of the detector elements in the detector array can be selectively controlled to function as a transmit detector element that functions to transmit a generated transmit signal in a radio or microwave frequency range or a visible light range of the electromagnetic spectrum into a target containing an analyte of interest. In addition, any one or more of the detector elements in the detector array can be selectively controlled to function as a receive detector element that functions to detect a response resulting from transmission of the transmit signal by the transmit detector element into the target. A scan routine can be implemented that includes a plurality of scans, where each scan uses a different combination of the detector elements to transmit a signal and detect a response. In the following description, a detector element, whether it is an antenna or a light emitting diode, that is controlled to function as a transmit detector element may simply be referred to as a transmit element, while a detector element, whether it is an antenna or a light emitting diode, that is controlled to function as a receive detector element may simply be referred to as a receive element.

When the detector elements in the detector array are antennas, the antennas, whether functioning as a transit antenna or as a receive antenna, are decoupled from one another which helps to improve the detection capability of the non-invasive analyte sensor. The decoupling between the antennas can be achieved using any one or more techniques that causes as much of the signal as possible that is transmitted by the transmit antenna to enter the target and that minimizes or even eliminates the amount of electromagnetic energy that is directly received by the receive antenna from the transmit antenna without traveling into the target. The decoupling can be achieved by one or more intentionally fabricated configurations and/or arrangements between the antennas that is sufficient to decouple the antennas from one another. In one non-limiting embodiment, the decoupling can be achieved by the antennas having intentionally different geometries from one another. Intentionally different geometries refers to different geometric configurations of the antennas that are intentional, and is distinct from differences in geometry of antennas that may occur by accident or unintentionally, for example due to manufacturing errors or tolerances.

Another technique to achieve decoupling of the antennas is to use an appropriate spacing between each antenna, depending upon factors such as output power, size of the antennas, frequency, and the presence of any shielding, so as to force a proportion of the electromagnetic lines of force of the transmit signal into the target so they reach the analyte, thereby minimizing or eliminating as much as possible direct receipt of electromagnetic energy by the receive antenna directly from the transmit antenna without traveling into the target. This technique helps to ensure that the response detected by the receive antenna is measuring the analyte and is not just the transmitted signal flowing directly from the transmit antenna to the receive antenna. In one embodiment, the sensor can use a first pair of transmit and receive antennas that have a first spacing therebetween, and a second pair of transmit and receive antennas that have a second spacing therebetween that differs from the first spacing.

The techniques described herein can be used to detect the presence of the analyte of interest, as well an amount of the analyte or a concentration of the analyte within the target. The techniques described herein can be used to detect a single analyte or more than one analyte. The target can be any target, for example human or non-human, animal or non-animal, biological or non-biological, that contains the analyte(s) that one may wish to detect. For example, the target can include, but is not limited to, human tissue, animal tissue, plant tissue, an inanimate object, soil, a fluid, genetic material, or a microbe. The analyte(s) can be any analyte, for example human or non-human, animal or non-animal, biological or non-biological, that one may wish to detect. For example, the analyte(s) can include, but is not limited to, one or more of blood glucose, blood alcohol, white blood cells, or luteinizing hormone.

In one embodiment, a non-invasive analyte sensor system described herein can include a detector array having at least two detector elements that can emit electromagnetic waves. A transmit circuit is selectively electrically connectable to any one or more of the at least two detector elements, with the transmit circuit being configured to generate at least one transmit signal to be transmitted into a target containing at least one analyte of interest by the one or more of the at least two detector elements the transmit circuit is electrically connected to. In addition, a receive circuit is selectively electrically connectable to any one or more of the at least two detector elements, and the receive circuit is configured to receive a response detected by the one or more of the at least two detector elements the receive circuit is electrically connected to resulting from transmission of the at least one transmit signal into the target containing the at least one analyte of interest.

In another embodiment, a non-invasive analyte sensor system can include an antenna array having at least two antennas. A transmit circuit is selectively electrically connectable to any one or more of the at least two antennas, where the transmit circuit is configured to generate at least one transmit signal to be transmitted into a target containing at least one analyte of interest by the one or more of the at least two antennas the transmit circuit is electrically connected to, and the at least one transmit signal is in a radio or microwave frequency range of the electromagnetic spectrum. In addition, a receive circuit is selectively electrically connectable to any one or more of the at least two antennas, where the receive circuit is configured to receive a response detected by the one or more of the at least two antennas the receive circuit is electrically connected to resulting from transmission of the at least one transmit signal into the target containing the at least one analyte of interest.

In one embodiment, the antenna array can be a decoupled antenna array and the at least two antennas can be decoupled from one another. The decoupling can be achieved by an intentional difference in geometry between the antennas. In another embodiment, decoupling can be achieved by arranging the antennas with an appropriate spacing therebetween that is sufficient to decouple the antennas.

In another embodiment described herein, a non-invasive analyte sensor system can include a sensor housing and a detector array attached to the sensor housing. The detector array has at least three decoupled elements each of which can act as an antenna, and the at least three decoupled elements have geometries that differ from one another. A transmit circuit is disposed in the sensor housing and is selectively electrically connectable to any one or more of the at least three elements, where the transmit circuit is configured to generate at least one transmit signal to be transmitted into a target containing at least one analyte of interest by the one or more of the at least three elements the transmit circuit is electrically connected to, and the at least one transmit signal is in a radio or microwave frequency range of the electromagnetic spectrum. In addition, a receive circuit is disposed in the sensor housing and is selectively electrically connectable to any one or more of the at least three elements, where the receive circuit is configured to receive a response detected by the one or more of the at least three elements the receive circuit is electrically connected to resulting from transmission of the at least one transmit signal into the target containing the at least one analyte of interest.

In still another embodiment described herein, a non-invasive analyte sensor system can include a sensor housing and an antenna array attached to the sensor housing. The antenna array has at least six decoupled antennas, where the at least six decoupled antennas have geometries that differ from one another, and the antenna array does not exceed 30.0 mm by 30.0 mm. A transmit circuit is disposed in the sensor housing and is selectively electrically connectable to any one or more of the at least six antennas. The transmit circuit is configured to generate at least one transmit signal to be transmitted into a target containing at least one analyte of interest by the one or more of the at least six antennas the transmit circuit is electrically connected to. The at least one transmit signal can have a plurality of different frequencies, and each one of the different frequencies is in a range of about 10 kHz to about 100 GHz. In addition, a receive circuit is disposed in the sensor housing and is selectively electrically connectable to any one or more of the at least six antennas. The receive circuit is configured to receive a response detected by the one or more of the at least six antennas the receive circuit is electrically connected to resulting from transmission of the at least one transmit signal into the target containing the at least one analyte of interest. One or more controllers disposed in the sensor housing controls electrical connection of the transmit circuit to the any one or more of the at least six antennas and also controls electrical connection of the receive circuit to the any one or more of the at least six antennas. In addition, a rechargeable battery is disposed in the sensor housing, with the rechargeable battery providing electrical power to power operation of the sensor system.

In another embodiment described herein, a method of non-invasive detection of an analyte includes, in a detector array having at least two detector elements, selectively connecting a transmit circuit to any one or more of the at least two detector elements of the detector array. At least one transmit signal is generated using the transmit circuit, with the at least one transmit signal being in a radio or microwave frequency or a visible light range of the electromagnetic spectrum. The at least one transmit signal is then transmitted into a target containing at least one analyte of interest using the one or more of the at least two detector elements connected to the transmit circuit. In addition, a receive circuit is selectively connected to a different one or more of the at least two detector elements of the detector array. The receive circuit and the different one or more of the at least two detector elements of the detector array are used to detect a response resulting from transmission of the at least one transmit signal into the target containing the at least one analyte of interest.

In another embodiment described herein, a method of non-invasive detection of an analyte includes, in a detector array having at least three decoupled elements each of which can act as an antenna and where the at least three decoupled elements have geometries that differ from one another, selectively connecting a transmit circuit to one element of the at least three elements of the antenna array. At least one transmit signal is generated using the transmit circuit, with the at least transmit signal having at least two different frequencies each of which falls within a range of between about 10 kHz to about 100 GHz. The at least one transmit signal is transmitted into a target containing at least one analyte of interest using the one element of the at least three elements connected to the transmit circuit. In addition, a receive circuit is selectively connected to one different element of the at least three elements of the detector array. The receive circuit and the one different element of the at least three elements of the detector array are used to detect a response resulting from transmission of the at least one transmit signal into the target containing the at least one analyte of interest.

In another embodiment described herein, a method of non-invasive detection of an analyte includes implementing a scan routine using a detector array that is electrically connected to a transmit circuit and electrically connected to a receive circuit, the detector array having at least three detector element. The scan routine includes, in a first scan, using a first combination of two or more of the at least three detector elements to transmit a first transmit signal that is in a radio or microwave frequency or visible range of the electromagnetic spectrum into a target containing at least one analyte of interest and to detect a response resulting from transmission of the first transmit signal into the target containing the at least one analyte of interest. In a second scan, a second combination of two or more of the at least three detector elements, different from the first combination, is used to transmit a second transmit signal that is in a radio or microwave frequency or visible range of the electromagnetic spectrum into the target containing the at least one analyte of interest and to detect a response resulting from transmission of the second transmit signal into the target containing the at least one analyte of interest.

In still another embodiment described herein, a method of non-invasive detection of an analyte includes implementing a scan routine using an antenna array that is electrically connected to a transmit circuit and electrically connected to a receive circuit, with the antenna array having at least three antennas that have geometries that differ from one another and the at least three antennas are decoupled from one another. The scan routine includes conducting a plurality of scans, with each scan using a different combination of two or more of the at least three antennas to transmit signals that are in a radio or microwave frequency range of the electromagnetic spectrum into a target containing at least one analyte of interest and to detect responses resulting from transmission of the signals into the target containing the at least one analyte of interest.

DRAWINGS

References are made to the accompanying drawings that form a part of this disclosure, and which illustrate embodiments in which the apparatus, systems and methods described in this specification can be practiced.

FIG. 1 is a schematic depiction of a non-invasive analyte sensor system with a non-invasive analyte sensor relative to a target according to an embodiment.

FIGS. 2A-C illustrate different example orientations of antenna arrays that can be used in the sensor system described herein.

FIG. 21A is a side view of the non-invasive analyte sensor of FIG. 20 using one example combination of light emitter and light detector.

FIG. 21B is another side view of the non-invasive analyte sensor of FIG. 20 using a second example combination of light emitter and light detector.

Like reference numbers represent like parts throughout.

DETAILED DESCRIPTION

Figure 1:
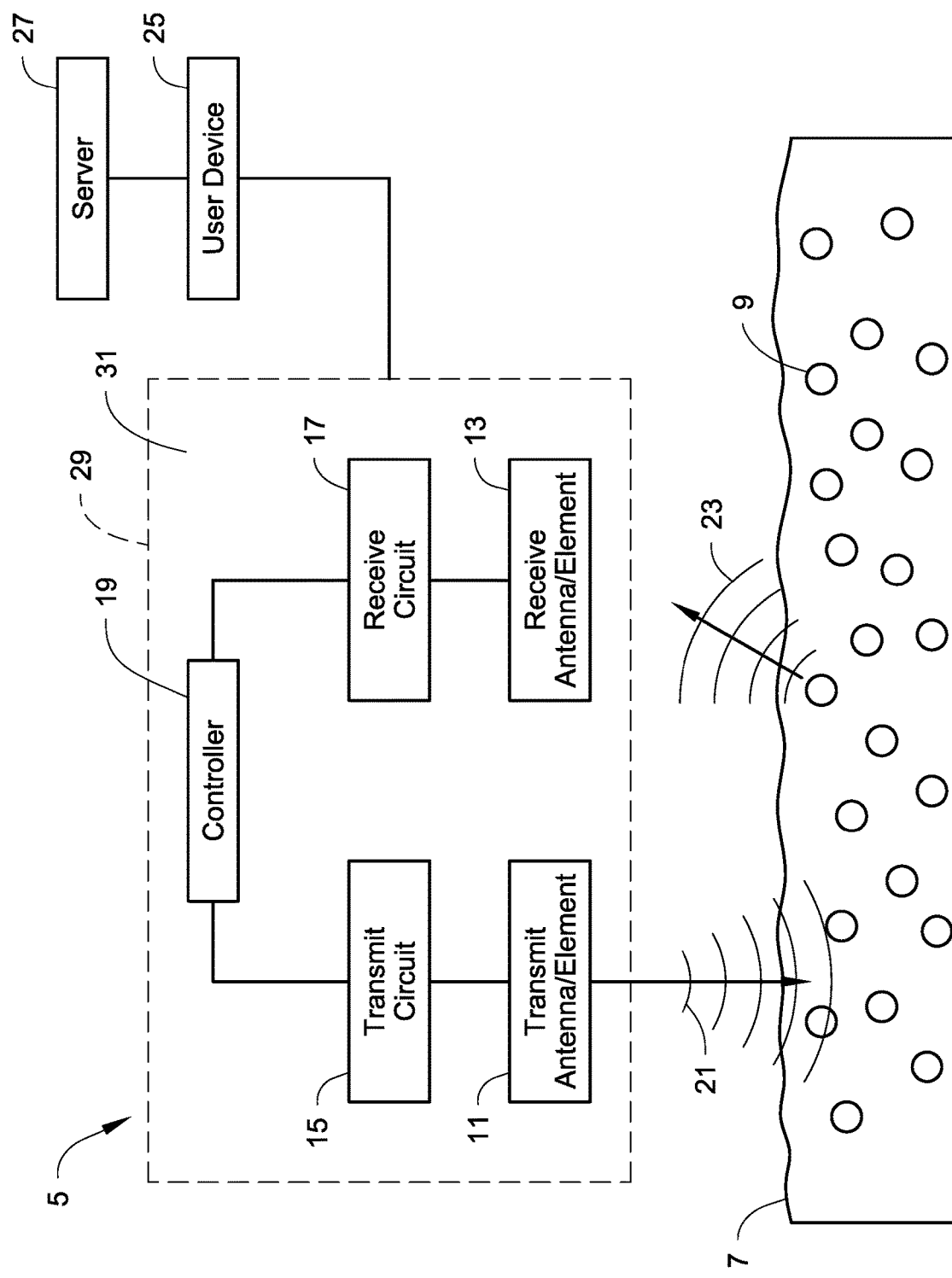

The following is a detailed description of apparatus, systems and methods of non-invasively detecting an analyte via spectroscopic techniques using non-optical frequencies such as in the radio or microwave frequency bands of the electromagnetic spectrum or optical frequencies in the visible range of the electromagnetic spectrum. A non-invasive analyte sensor includes at least one detector element that functions as a transmit detector element (which may also be referred to as a transmit element) and that functions to transmit a generated transmit signal that is in a radio or microwave frequency or visible range of the electromagnetic spectrum into a target containing an analyte of interest, and at least one detector element that functions as a receive detector element (which may also be referred to as a receive element) and that functions to detect a response resulting from transmission of the transmit signal by the transmit detector element into the target. When the detector elements are antennas, transmit antenna and the receive antenna are decoupled from one another which improves the detection performance of the sensor.

The following description together with FIGS. 1-19 will initially describe the detector elements as being antennas and the detector array that includes the antenna as an antenna array. Later in the following description, together with FIGS. 20-21A-B, the detector elements will be described as being light emitting devices such as light emitting diodes (LEDs) and the detector array that includes the LED as an LED array.

The transmit antenna and the receive antenna can be located near the target and operated as further described herein to assist in detecting at least one analyte in the target. The transmit antenna transmits a signal, which has at least two frequencies in the radio or microwave frequency range, toward and into the target. The signal with the at least two frequencies can be formed by separate signal portions, each having a discrete frequency, that are transmitted separately at separate times at each frequency. In another embodiment, the signal with the at least two frequencies may be part of a complex signal that includes a plurality of frequencies including the at least two frequencies. The complex signal can be generated by blending or multiplexing multiple signals together followed by transmitting the complex signal whereby the plurality of frequencies are transmitted at the same time. One possible technique for generating the complex signal includes, but is not limited to, using an inverse Fourier transformation technique. The receive antenna detects a response resulting from transmission of the signal by the transmit antenna into the target containing the at least one analyte of interest.

The transmit antenna and the receive antenna are decoupled (which may also be referred to as detuned or the like) from one another. Decoupling refers to intentionally fabricating the configuration and/or arrangement of the transmit antenna and the receive antenna to minimize direct communication between the transmit antenna and the receive antenna, preferably absent shielding. Shielding between the transmit antenna and the receive antenna can be utilized. However, the transmit antenna and the receive antenna are decoupled even without the presence of shielding.

The signal(s) detected by the receive antenna can be analyzed to detect the analyte based on the intensity of the received signal(s) and reductions in intensity at one or more frequencies where the analyte absorbs the transmitted signal. An example of detecting an analyte using a non-invasive spectroscopy sensor operating in the radio or microwave frequency range of the electromagnetic spectrum is described in WO 2019/217461, the entire contents of which are incorporated herein by reference. The signal(s) detected by the receive antenna can be complex signals including a plurality of signal components, each signal component being at a different frequency. In an embodiment, the detected complex signals can be decomposed into the signal components at each of the different frequencies, for example through a Fourier transformation. In an embodiment, the complex signal detected by the receive antenna can be analyzed as a whole (i.e. without demultiplexing the complex signal) to detect the analyte as long as the detected signal provides enough information to make the analyte detection. In addition, the signal(s) detected by the receive antenna can be separate signal portions, each having a discrete frequency.

In one embodiment, the sensor described herein can be used to detect the presence of at least one analyte in a target. In another embodiment, the sensor described herein can detect an amount or a concentration of the at least one analyte in the target. The target can be any target containing at least one analyte of interest that one may wish to detect. The target can be human or non-human, animal or non-animal, biological or non-biological. For example, the target can include, but is not limited to, human tissue, animal tissue, plant tissue, an inanimate object, soil, a fluid, genetic material, or a microbe. Non-limiting examples of targets include, but are not limited to, a fluid, for example blood, interstitial fluid, cerebral spinal fluid, lymph fluid or urine, human tissue, animal tissue, plant tissue, an inanimate object, soil, genetic material, or a microbe.

The analyte(s) can be any analyte that one may wish to detect. The analyte can be human or non-human, animal or non-animal, biological or non-biological. For example, the analyte(s) can include, but is not limited to, one or more of blood glucose, blood alcohol, white blood cells, or luteinizing hormone. The analyte(s) can include, but is not limited to, a chemical, a combination of chemicals, a virus, a bacteria, or the like. The analyte can be a chemical included in another medium, with non-limiting examples of such media including a fluid containing the at least one analyte, for example blood, interstitial fluid, cerebral spinal fluid, lymph fluid or urine, human tissue, animal tissue, plant tissue, an inanimate object, soil, genetic material, or a microbe. The analyte(s) may also be a non-human, non-biological particle such as a mineral or a contaminant.

The analyte(s) can include, for example, naturally occurring substances, artificial substances, metabolites, and/or reaction products. As non-limiting examples, the at least one analyte can include, but is not limited to, insulin, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free (3-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, polio virus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

The analyte(s) can also include one or more chemicals introduced into the target. The analyte(s) can include a marker such as a contrast agent, a radioisotope, or other chemical agent. The analyte(s) can include a fluorocarbon-based synthetic blood. The analyte(s) can include a drug or pharmaceutical composition, with non-limiting examples including ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The analyte(s) can include other drugs or pharmaceutical compositions. The analyte(s) can include neurochemicals or other chemicals generated within the body, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

Referring now to FIG. 1, an embodiment of a non-invasive analyte sensor system with a non-invasive analyte sensor 5 is illustrated. The sensor 5 is depicted relative to a target 7 that contains an analyte of interest 9. In this example, the sensor 5 is depicted as including an antenna array that includes a transmit antenna/element 11 (hereinafter "transmit antenna 11") and a receive antenna/element 13 (hereinafter "receive antenna 13"). The sensor 5 further includes a transmit circuit 15, a receive circuit 17, and a controller 19. As discussed further below, the sensor 5 can also include a power supply, such as a battery (not shown in FIG. 1). In some embodiments, power can be provided from mains power, for example by plugging the sensor 5 into a wall socket via a cord connected to the sensor 5.

The transmit antenna 11 is positioned, arranged and configured to transmit a signal 21 that is the radio frequency (RF) or microwave range of the electromagnetic spectrum into the target 7. The transmit antenna 11 can be an electrode or any other suitable transmitter of electromagnetic signals in the radio frequency (RF) or microwave range. The transmit antenna 11 can have any arrangement and orientation relative to the target 7 that is sufficient to allow the analyte sensing to take place. In one non-limiting embodiment, the transmit antenna 11 can be arranged to face in a direction that is substantially toward the target 7.

The signal 21 transmitted by the transmit antenna 11 is generated by the transmit circuit 15 which is electrically connectable to the transmit antenna 11. The transmit circuit 15 can have any configuration that is suitable to generate a transmit signal to be transmitted by the transmit antenna 11. Transmit circuits for generating transmit signals in the RF or microwave frequency range are well known in the art. In one embodiment, the transmit circuit 15 can include, for example, a connection to a power source, a frequency generator, and optionally filters, amplifiers or any other suitable elements for a circuit generating an RF or microwave frequency electromagnetic signal. In an embodiment, the signal generated by the transmit circuit 15 can have at least two discrete frequencies (i.e. a plurality of discrete frequencies), each of which is in the range from about 10 kHz to about 100 GHz. In another embodiment, each of the at least two discrete frequencies can be in a range from about 300 MHz to about 6000 MHz. In an embodiment, the transmit circuit 15 can be configured to sweep through a range of frequencies that are within the range of about 10 kHz to about 100 GHz, or in another embodiment a range of about 300 MHz to about 6000 MHz. In an embodiment, the transmit circuit 15 can be configured to produce a complex transmit signal, the complex signal including a plurality of signal components, each of the signal components having a different frequency. The complex signal can be generated by blending or multiplexing multiple signals together followed by transmitting the complex signal whereby the plurality of frequencies are transmitted at the same time.

The receive antenna 13 is positioned, arranged, and configured to detect one or more electromagnetic response signals 23 that result from the transmission of the transmit signal 21 by the transmit antenna 11 into the target 7 and impinging on the analyte 9. The receive antenna 13 can be an electrode or any other suitable receiver of electromagnetic signals in the radio frequency (RF) or microwave range. In an embodiment, the receive antenna 13 is configured to detect electromagnetic signals having at least two frequencies, each of which is in the range from about 10 kHz to about 100 GHz, or in another embodiment a range from about 300 MHz to about 6000 MHz. The receive antenna 13 can have any arrangement and orientation relative to the target 7 that is sufficient to allow detection of the response signal(s) 23 to allow the analyte sensing to take place. In one non-limiting embodiment, the receive antenna 13 can be arranged to face in a direction that is substantially toward the target 7.

The receive circuit 17 is electrically connectable to the receive antenna 13 and conveys the received response from the receive antenna 13 to the controller 19. The receive circuit 17 can have any configuration that is suitable for interfacing with the receive antenna 13 to convert the electromagnetic energy detected by the receive antenna 13 into one or more signals reflective of the response signal(s) 23. The construction of receive circuits are well known in the art. The receive circuit 17 can be configured to condition the signal(s) prior to providing the signal(s) to the controller 19, for example through amplifying the signal(s), filtering the signal(s), or the like. Accordingly, the receive circuit 17 may include filters, amplifiers, or any other suitable components for conditioning the signal(s) provided to the controller 19. In an embodiment, at least one of the receive circuit 17 or the controller 19 can be configured to decompose or demultiplex a complex signal, detected by the receive antenna 13, including a plurality of signal components each at different frequencies into each of the constituent signal components. In an embodiment, decomposing the complex signal can include applying a Fourier transform to the detected complex signal. However, decomposing or demultiplexing a received complex signal is optional. Instead, in an embodiment, the complex signal detected by the receive antenna can be analyzed as a whole (i.e. without demultiplexing the complex signal) to detect the analyte as long as the detected signal provides enough information to make the analyte detection.

The controller 19 controls the operation of the sensor 5. The controller 19, for example, can direct the transmit circuit 15 to generate a transmit signal to be transmitted by the transmit antenna 11. The controller 19 further receives signals from the receive circuit 17. The controller 19 can optionally process the signals from the receive circuit 17 to detect the analyte(s) 9 in the target 7. In one embodiment, the controller 19 may optionally be in communication with at least one external device 25 such as a user device and/or a remote server 27, for example through one or more wireless connections such as Bluetooth, wireless data connections such a 4G, 5G, LTE or the like, or Wi-Fi. If provided, the external device 25 and/or remote server 27 may process (or further process) the signals that the controller 19 receives from the receive circuit 17, for example to detect the analyte(s) 9. If provided, the external device 25 may be used to provide communication between the sensor 5 and the remote server 27, for example using a wired data connection or via a wireless data connection or Wi-Fi of the external device 25 to provide the connection to the remote server 27.

With continued reference to FIG. 1, the sensor 5 may include a sensor housing 29 (shown in dashed lines) that defines an interior space 31. Components of the sensor 5 may be attached to and/or disposed within the housing 29. For example, the transmit antenna 11 and the receive antenna 13 are attached to the housing 29. In some embodiments, the antennas 11, 13 may be entirely or partially within the interior space 31 of the housing 29. In some embodiments, the antennas 11, 13 may be attached to the housing 29 but at least partially or fully located outside the interior space 31. In some embodiments, the transmit circuit 15, the receive circuit 17 and the controller 19 are attached to the housing 29 and disposed entirely within the sensor housing 29.

The receive antenna 13 is decoupled or detuned with respect to the transmit antenna 11 such that electromagnetic coupling between the transmit antenna 11 and the receive antenna 13 is reduced. The decoupling of the transmit antenna 11 and the receive antenna 13 increases the portion of the signal(s) detected by the receive antenna 13 that is the response signal(s) 23 from the target 7, and minimizes direct receipt of the transmitted signal 21 by the receive antenna 13. The decoupling of the transmit antenna 11 and the receive antenna 13 results in transmission from the transmit antenna 11 to the receive antenna 13 having a reduced forward gain ($S_{21}$) and an increased reflection at output ($S_{22}$) compared to antenna systems having coupled transmit and receive antennas.

In an embodiment, coupling between the transmit antenna 11 and the receive antenna 13 is 95% or less. In another embodiment, coupling between the transmit antenna 11 and the receive antenna 13 is 90% or less. In another embodiment, coupling between the transmit antenna 11 and the receive antenna 13 is 85% or less. In another embodiment, coupling between the transmit antenna 11 and the receive antenna 13 is 75% or less.

Any technique for reducing coupling between the transmit antenna 11 and the receive antenna 13 can be used. For example, the decoupling between the transmit antenna 11 and the receive antenna 13 can be achieved by one or more intentionally fabricated configurations and/or arrangements between the transmit antenna 11 and the receive antenna 13 that is sufficient to decouple the transmit antenna 11 and the receive antenna 13 from one another.

For example, in one embodiment described further below, the decoupling of the transmit antenna 11 and the receive antenna 13 can be achieved by intentionally configuring the transmit antenna 11 and the receive antenna 13 to have different geometries from one another. Intentionally different geometries refers to different geometric configurations of the transmit and receive antennas 11, 13 that are intentional. Intentional differences in geometry are distinct from differences in geometry of transmit and receive antennas that may occur by accident or unintentionally, for example due to manufacturing errors or tolerances.

Another technique to achieve decoupling of the transmit antenna 11 and the receive antenna 13 is to provide appropriate spacing between each antenna 11, 13 that is sufficient to decouple the antennas 11, 13 and force a proportion of the electromagnetic lines of force of the transmitted signal 21 into the target 7 thereby minimizing or eliminating as much as possible direct receipt of electromagnetic energy by the receive antenna 13 directly from the transmit antenna 11 without traveling into the target 7. The appropriate spacing between each antenna 11, 13 can be determined based upon factors that include, but are not limited to, the output power of the signal from the transmit antenna 11, the size of the antennas 11, 13, the frequency or frequencies of the transmitted signal, and the presence of any shielding between the antennas. This technique helps to ensure that the response detected by the receive antenna 13 is measuring the analyte 9 and is not just the transmitted signal 21 flowing directly from the transmit antenna 11 to the receive antenna 13. In some embodiments, the appropriate spacing between the antennas 11, 13 can be used together with the intentional difference in geometries of the antennas 11, 13 to achieve decoupling.

In one embodiment, the transmit signal that is transmitted by the transmit antenna 11 can have at least two different frequencies, for example upwards of 7 to 12 different and discrete frequencies. In another embodiment, the transmit signal can be a series of discrete, separate signals with each separate signal having a single frequency or multiple different frequencies.

In one embodiment, the transmit signal (or each of the transmit signals) can be transmitted over a transmit time that is less than, equal to, or greater than about 300 ms. In another embodiment, the transmit time can be than, equal to, or greater than about 200 ms. In still another embodiment, the transmit time can be less than, equal to, or greater than about 30 ms. The transmit time could also have a magnitude that is measured in seconds, for example 1 second, 5 seconds, 10 seconds, or more. In an embodiment, the same transmit signal can be transmitted multiple times, and then the transmit time can be averaged. In another embodiment, the transmit signal (or each of the transmit signals) can be transmitted with a duty cycle that is less than or equal to about 50%.

FIGS. 2A-2C illustrate examples of antenna arrays 33 that can be used in the sensor system 5 and how the antenna arrays 33 can be oriented. Many orientations of the antenna arrays 33 are possible, and any orientation can be used as long as the sensor 5 can perform its primary function of sensing the analyte 9.

In FIG. 2A, the antenna array 33 includes the transmit antenna 11 and the receive antenna 13 disposed on a substrate 35 which may be substantially planar. This example depicts the array 33 disposed substantially in an X-Y plane. In this example, dimensions of the antennas 11, 13 in the X and Y-axis directions can be considered lateral dimensions, while a dimension of the antennas 11, 13 in the Z-axis direction can be considered a thickness dimension. In this example, each of the antennas 11, 13 has at least one lateral dimension (measured in the X-axis direction and/or in the Y-axis direction) that is greater than the thickness dimension thereof (in the Z-axis direction). In other words, the transmit antenna 11 and the receive antenna 13 are each relatively flat or of relatively small thickness in the Z-axis direction compared to at least one other lateral dimension measured in the X-axis direction and/or in the Y-axis direction.

In use of the embodiment in FIG. 2A, the sensor and the array 33 may be positioned relative to the target 7 such that the target 7 is below the array 33 in the Z-axis direction or above the array 33 in the Z-axis direction whereby one of the faces of the antennas 11, 13 face toward the target 7. Alternatively, the target 7 can be positioned to the left or right sides of the array 33 in the X-axis direction whereby one of the ends of each one of the antennas 11, 13 face toward the target 7. Alternatively, the target 7 can be positioned to the sides of the array 33 in the Y-axis direction whereby one of the sides of each one of the antennas 11, 13 face toward the target 7.

The sensor 5 can also be provided with one or more additional antenna arrays in addition the antenna array 33. For example, FIG. 2A also depicts an optional second antenna array 33a that includes the transmit antenna 11 and the receive antenna 13 disposed on a substrate 35a which may be substantially planar. Like the array 33, the array 33a may also be disposed substantially in the X-Y plane, with the arrays 33, 33a spaced from one another in the X-axis direction.

In FIG. 2B, the antenna array 33 is depicted as being disposed substantially in the Y-Z plane. In this example, dimensions of the antennas 11, 13 in the Y and Z-axis directions can be considered lateral dimensions, while a dimension of the antennas 11, 13 in the X-axis direction can be considered a thickness dimension. In this example, each of the antennas 11, 13 has at least one lateral dimension (measured in the Y-axis direction and/or in the Z-axis direction) that is greater than the thickness dimension thereof (in the X-axis direction). In other words, the transmit antenna 11 and the receive antenna 13 are each relatively flat or of relatively small thickness in the X-axis direction compared to at least one other lateral dimension measured in the Y-axis direction and/or in the Z-axis direction.

In use of the embodiment in FIG. 2B, the sensor and the array 33 may be positioned relative to the target 7 such that the target 7 is below the array 33 in the Z-axis direction or above the array 33 in the Z-axis direction whereby one of the ends of each one of the antennas 11, 13 face toward the target 7. Alternatively, the target 7 can be positioned in front of or behind the array 33 in the X-axis direction whereby one of the faces of each one of the antennas 11, 13 face toward the target 7. Alternatively, the target 7 can be positioned to one of the sides of the array 33 in the Y-axis direction whereby one of the sides of each one of the antennas 11, 13 face toward the target 7.

In FIG. 2C, the antenna array 33 is depicted as being disposed substantially in the X-Z plane. In this example, dimensions of the antennas 11, 13 in the X and Z-axis directions can be considered lateral dimensions, while a dimension of the antennas 11, 13 in the Y-axis direction can be considered a thickness dimension. In this example, each of the antennas 11, 13 has at least one lateral dimension (measured in the X-axis direction and/or in the Z-axis direction) that is greater than the thickness dimension thereof (in the Y-axis direction). In other words, the transmit antenna 11 and the receive antenna 13 are each relatively flat or of relatively small thickness in the Y-axis direction compared to at least one other lateral dimension measured in the X-axis direction and/or in the Z-axis direction.

In use of the embodiment in FIG. 2C, the sensor and the array 33 may be positioned relative to the target 7 such that the target 7 is below the array 33 in the Z-axis direction or above the array 33 in the Z-axis direction whereby one of the ends of each one of the antennas 11, 13 face toward the target 7. Alternatively, the target 7 can be positioned to the left or right sides of the array 33 in the X-axis direction whereby one of the sides of each one of the antennas 11, 13 face toward the target 7. Alternatively, the target 7 can be positioned in front of or in back of the array 33 in the Y-axis direction whereby one of the faces of each one of the antennas 11, 13 face toward the target 7.

The arrays 33, 33a in FIGS. 2A-2C need not be oriented entirely within a plane such as the X-Y plane, the Y-Z plane or the X-Z plane. Instead, the arrays 33, 33a can be disposed at angles to the X-Y plane, the Y-Z plane and the X-Z plane.

Decoupling Antennas Using Differences in Antenna Geometries

As mentioned above, one technique for decoupling the transmit antenna 11 from the receive antenna 13 is to intentionally configure the transmit antenna 11 and the receive antenna 13 to have intentionally different geometries. Intentionally different geometries refers to differences in geometric configurations of the transmit and receive antennas 11, 13 that are intentional, and is distinct from differences in geometry of the transmit and receive antennas 11, 13 that may occur by accident or unintentionally, for example due to manufacturing errors or tolerances when fabricating the antennas 11, 13.

The different geometries of the antennas 11, 13 may manifest itself, and may be described, in a number of different ways. For example, in a plan view of each of the antennas 11, 13 (such as in FIGS. 3A-I), the shapes of the perimeter edges of the antennas 11, 13 may be different from one another. The different geometries may result in the antennas 11, 13 having different surface areas in plan view. The different geometries may result in the antennas 11, 13 having different aspect ratios in plan view (i.e. a ratio of their sizes in different dimensions; for example, as discussed in further detail below, the ratio of the length divided by the width of the antenna 11 may be different than the ratio of the length divided by the width for the antenna 13). In some embodiments, the different geometries may result in the antennas 11, 13 having any combination of different perimeter edge shapes in plan view, different surface areas in plan view, and/or different aspect ratios. In some embodiments, the antennas 11, 13 may have one or more holes formed therein (see FIG. 2B) within the perimeter edge boundary, or one or more notches formed in the perimeter edge (see FIG. 2B).

So as used herein, a difference in geometry or a difference in geometrical shape of the antennas 11, 13 refers to any intentional difference in the figure, length, width, size, shape, area closed by a boundary (i.e. the perimeter edge), etc. when the respective antenna 11, 13 is viewed in a plan view.

The antennas 11, 13 can have any configuration and can be formed from any suitable material that allows them to perform the functions of the antennas 11, 13 as described herein. In one embodiment, the antennas 11, 13 can be formed by strips of material. A strip of material can include a configuration where the strip has at least one lateral dimension thereof greater than a thickness dimension thereof when the antenna is viewed in a plan view (in other words, the strip is relatively flat or of relatively small thickness compared to at least one other lateral dimension, such as length or width when the antenna is viewed in a plan view as in FIGS. 3A-I). A strip of material can include a wire. The antennas 11, 13 can be formed from any suitable conductive material(s) including metals and conductive non-metallic materials. Examples of metals that can be used include, but are not limited to, copper or gold. Another example of a material that can be used is non-metallic materials that are doped with metallic material to make the non-metallic material conductive.

In FIGS. 2A-2C, the antennas 11, 13 within each one of the arrays 33, 33a have different geometries from one another. In addition, FIGS. 3A-I illustrate plan views of additional examples of the antennas 11, 13 having different geometries from one another. The examples in FIGS. 2A-2C and 3A-I are not exhaustive and many different configurations are possible.

Figure 3A:
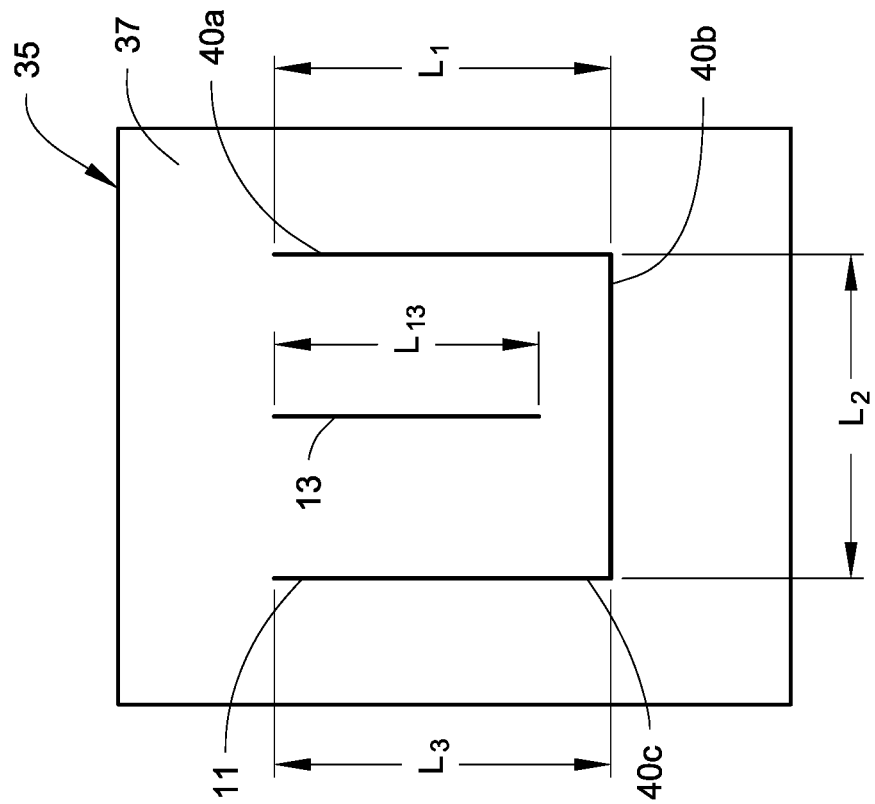
FIGS. 3A-3I illustrate different examples of transmit and receive antennas with different geometries.

With reference initially to FIG. 3A, a plan view of an antenna array having two antennas with different geometries is illustrated. In this example (as well as for the examples in FIGS. 2A-2C and 3B-3I), for sake of convenience in describing the concepts herein, one antenna is labeled as the transmit antenna 11 and the other antenna is labeled as the receive antenna 13. However, the antenna labeled as the transmit antenna 11 could be the receive antenna 13, while the antenna labeled as the receive antenna 13 could be the transmit antenna 11. Each of the antennas 11, 13 are disposed on the substrate 35 having a planar surface 37.

The antennas 11, 13 can be formed as linear strips or traces on the surface 37. In this example, the antenna 11 is generally U-shaped and has a first linear leg 40a, a second linear leg 40b that extends perpendicular to the first leg 40a, and a third linear leg 40c that extends parallel to the leg 40a. Likewise, the antenna 13 is formed by a single leg that extends parallel to, and between, the legs 40a, 40c.

In the example depicted in FIG. 3A, each one of the antennas 11, 13 has at least one lateral dimension that is greater than a thickness dimension thereof (in FIG. 3A, the thickness dimension would extend into/from the page when viewing FIG. 3A). For example, the leg 40a of the antenna 11 extends in one direction (i.e. a lateral dimension) an extent that is greater than a thickness dimension of the leg 40a extending into or out of the page; the leg 40b of the antenna 11 extends in a direction (i.e. a lateral dimension) an extent that is greater than a thickness dimension of the leg 40b extending into or out of the page; and the leg 40c of the antenna 11 extends in one direction (i.e. a lateral dimension) an extent that is greater than a thickness dimension of the leg 40c extending into or out of the page. Likewise, the antenna 13 extends in one direction (i.e. a lateral dimension) an extent that is greater than a thickness dimension of the antenna 13 extending into or out of the page.

The antennas 11, 13 also differ in geometry from one another in that the total linear length of the antenna 11 (determined by adding the individual lengths $L_1$, $L_2$, $L_3$ of the legs 40a-c together) when viewed in plan view is greater than the length $L_{13}$ of the antenna 13 when viewed in plan view.

Figure 3B:
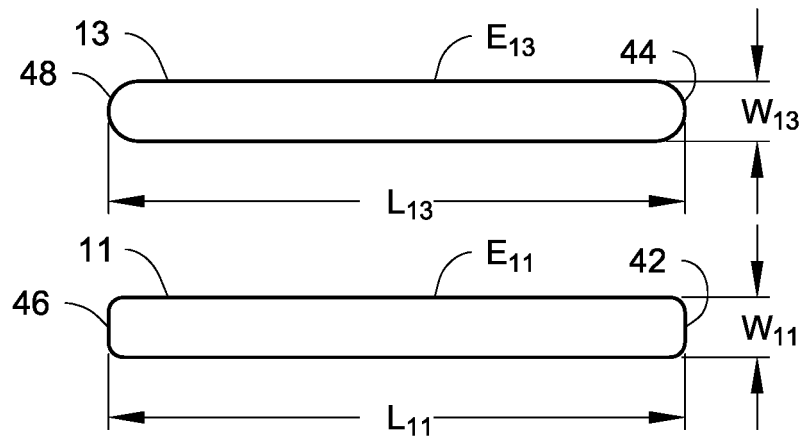

FIG. 3B illustrates another plan view of an antenna array having two antennas with different geometries. In this example, the antennas 11, 13 are illustrated as substantially linear strips each with a lateral length $L_{11}$, $L_{13}$, a lateral width $W_{11}$, $W_{13}$, and a perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3B. In this example, the antennas 11, 13 differ in geometry from one another in that the shapes of the ends of the antennas 11, 13 differ from one another. For example, when viewing FIG. 3B, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. It is also possible that the lateral lengths $L_{11}$, $L_{13}$ and/or the lateral widths $W_{11}$, $W_{13}$ of the antennas 11, 13 could differ from one another.

Figure 3C:
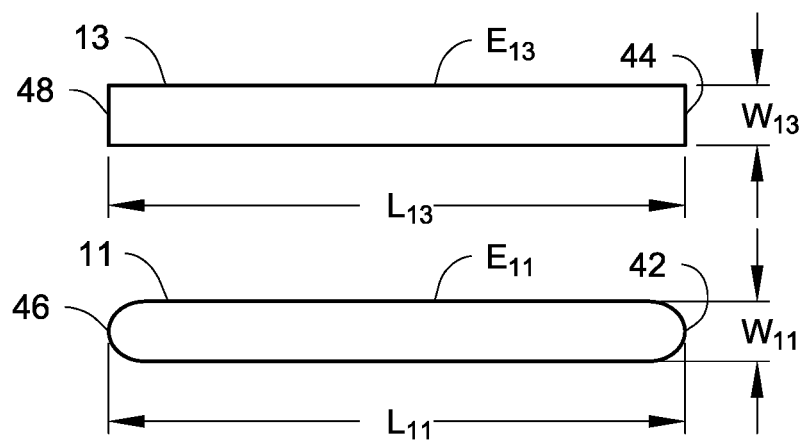

FIG. 3C illustrates another plan view of an antenna array having two antennas with different geometries that is somewhat similar to FIG. 3B. In this example, the antennas 11, 13 are illustrated as substantially linear strips each with the lateral length $L_{11}$, $L_{13}$, the lateral width $W_{11}$, $W_{13}$, and the perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3C. In this example, the antennas 11, 13 differ in geometry from one another in that the shapes of the ends of the antennas 11, 13 differ from one another. For example, when viewing FIG. 3C, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. In addition, the lateral widths $W_{11}$, $W_{13}$ of the antennas 11, 13 differ from one another. It is also possible that the lateral lengths $L_{11}$, $L_{13}$ of the antennas 11, 13 could differ from one another.

Figure 3D:
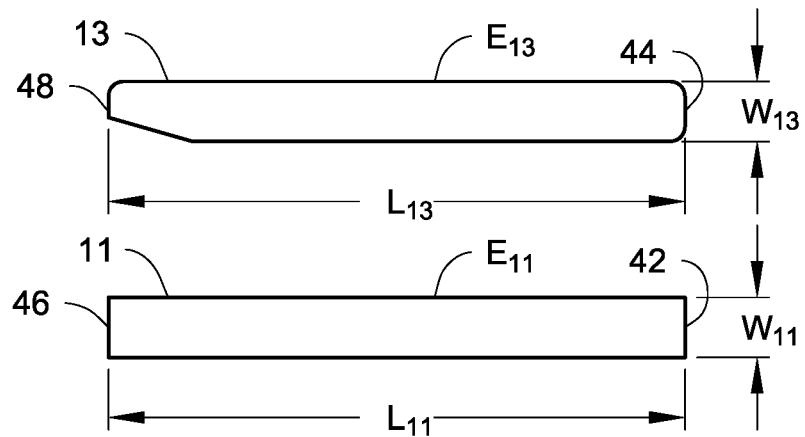

FIG. 3D illustrates another plan view of an antenna array having two antennas with different geometries that is somewhat similar to FIGS. 3B and 3C. In this example, the antennas 11, 13 are illustrated as substantially linear strips each with the lateral length $L_{11}$, $L_{13}$, the lateral width $W_{11}$, $W_{13}$, and the perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3D. In this example, the antennas 11, 13 differ in geometry from one another in that the shapes of the ends of the antennas 11, 13 differ from one another. For example, when viewing FIG. 3D, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. In addition, the lateral widths $W_{11}$, $W_{13}$ of the antennas 11, 13 differ from one another. It is also possible that the lateral lengths $L_{11}$, $L_{13}$ of the antennas 11, 13 could differ from one another.

Figure 3F:
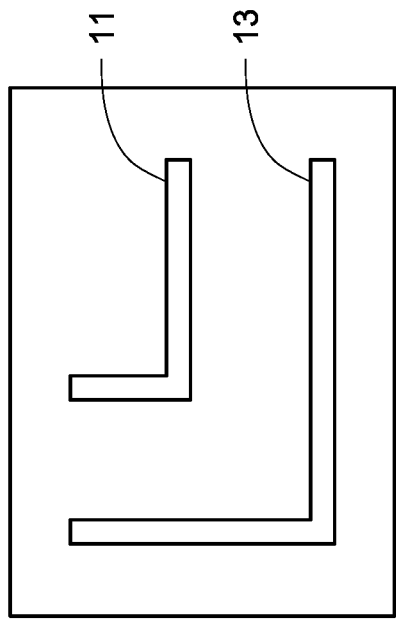
Figure 3G:
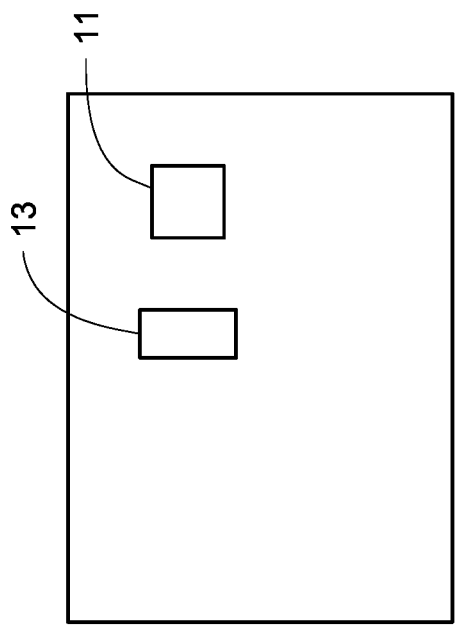
Figure 3E:
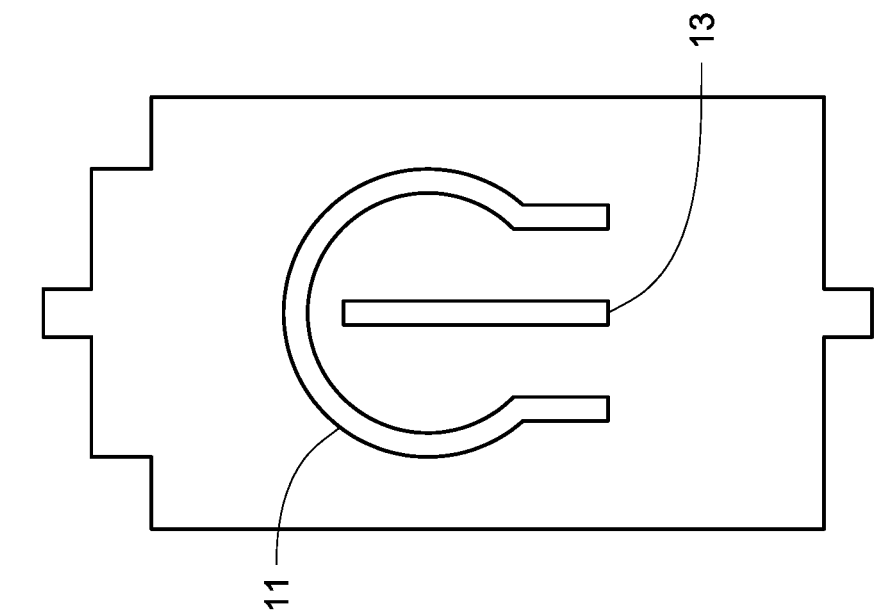

FIG. 3E illustrates another plan view of an antenna array having two antennas with different geometries on a substrate. In this example, the antenna 11 is illustrated as being a strip of material having a generally horseshoe shape, while the antenna 13 is illustrated as being a strip of material that is generally linear. The planar shapes (i.e. geometries) of the antennas 11, 13 differ from one another. In addition, the total length of the antenna 11 (measured from one end to the other) when viewed in plan view is greater than the length of the antenna 13 when viewed in plan.

FIG. 3F illustrates another plan view of an antenna array having two antennas with different geometries on a substrate. In this example, the antenna 11 is illustrated as being a strip of material forming a right angle, and the antenna 13 is also illustrated as being a strip of material that forms a larger right angle. The planar shapes (i.e. geometries) of the antennas 11, 13 differ from one another since the total area in plan view of the antenna 13 is greater than the total area in plan view of the antenna 11. In addition, the total length of the antenna 11 (measured from one end to the other) when viewed in plan view is less than the length of the antenna 13 when viewed in plan.

FIG. 3G illustrates another plan view of an antenna array having two antennas with different geometries on a substrate. In this example, the antenna 11 is illustrated as being a strip of material forming a square, and the antenna 13 is illustrated as being a strip of material that forms a rectangle. The planar shapes (i.e. geometries) of the antennas 11, 13 differ from one another. In addition, at least one of the width/length of the antenna 11 when viewed in plan view is less than one of the width/length of the antenna 13 when viewed in plan.

Figure 3I:
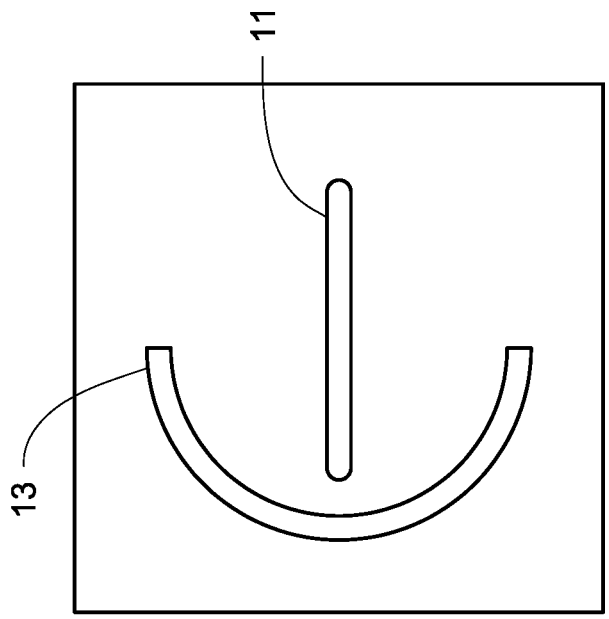
Figure 3H:
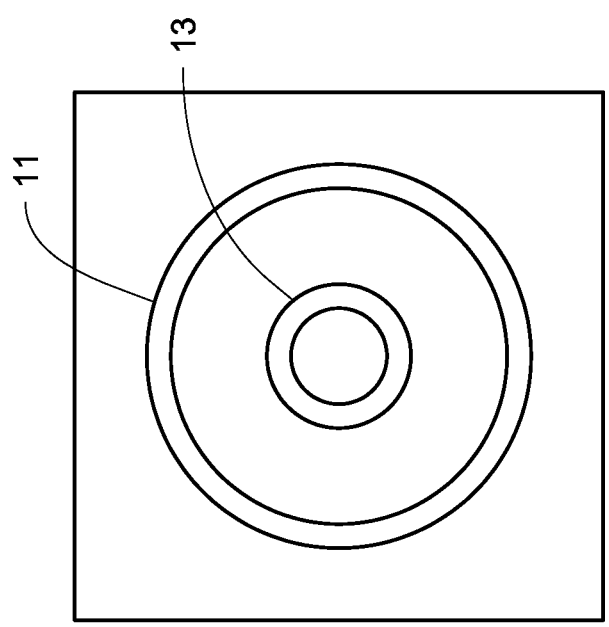

FIG. 3H illustrates another plan view of an antenna array having two antennas with different geometries on a substrate. In this example, the antenna 11 is illustrated as being a strip of material forming a circle when viewed in plan, and the antenna 13 is also illustrated as being a strip of material that forms a smaller circle when viewed in plan surrounded by the circle formed by the antenna 11. The planar shapes (i.e. geometries) of the antennas 11, 13 differ from one another due to the different sizes of the circles.

FIG. 3I illustrates another plan view of an antenna array having two antennas with different geometries on a substrate. In this example, the antenna 11 is illustrated as being a linear strip of material, and the antenna 13 is illustrated as being a strip of material that forms a semi-circle when viewed in plan. The planar shapes (i.e. geometries) of the antennas 11, 13 differ from one another due to the different shapes/geometries of the antennas 11, 13.

Figure 4A:
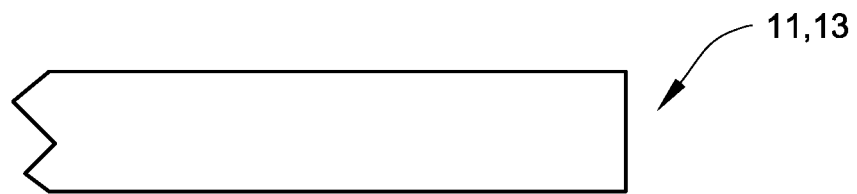
FIGS. 4A, 4B, 4C and 4D illustrate additional examples of different shapes that the ends of the transmit and receive antennas can have.
Figure 4B:
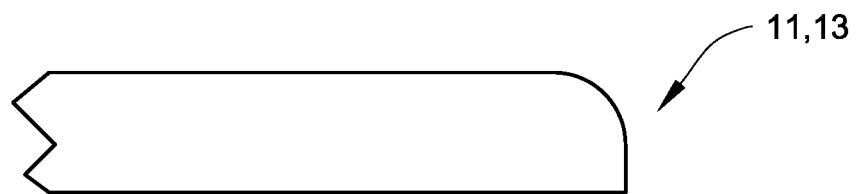
Figure 4C:
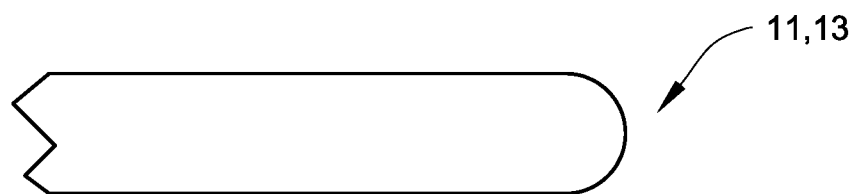
Figure 4D:
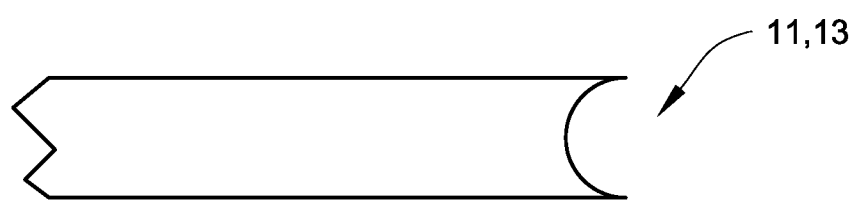

FIG. 4A-D are plan views of additional examples of different shapes that the ends of the transmit and receive antennas 11, 13 can have to achieve differences in geometry. Either one of, or both of, the ends of the antennas 11, 13 can have the shapes in FIGS. 4A-D, including in the embodiments in FIGS. 3A-I. FIG. 4A depicts the end as being generally rectangular. FIG. 4B depicts the end as having one rounded corner while the other corner remains a right angle. FIG. 4C depicts the entire end as being rounded or outwardly convex. FIG. 4D depicts the end as being inwardly concave. Many other shapes are possible.

Another technique to achieve decoupling of the antennas 11, 13 is to use an appropriate spacing between each antenna 11, 13 with the spacing being sufficient to force most or all of the signal(s) transmitted by the transmit antenna 11 into the target, thereby minimizing the direct receipt of electromagnetic energy by the receive antenna 13 directly from the transmit antenna 11. The appropriate spacing can be used by itself to achieve decoupling of the antennas 11, 13. In another embodiment, the appropriate spacing can be used together with differences in geometry of the antennas 11, 13 to achieve decoupling.

Referring to FIG. 2A, there is a spacing D between the transmit antenna 11 and the receive antenna 13 at the location indicated. The spacing D between the antennas 11, 13 may be constant over the entire length (for example in the X-axis direction) of each antenna 11, 13, or the spacing D between the antennas 11, 13 could vary. Any spacing D can be used as long as the spacing D is sufficient to result in most or all of the signal(s) transmitted by the transmit antenna 11 reaching the target and minimizing the direct receipt of electromagnetic energy by the receive antenna 13 directly from the transmit antenna 11, thereby decoupling the antennas 11, 13 from one another.

Figure 5:
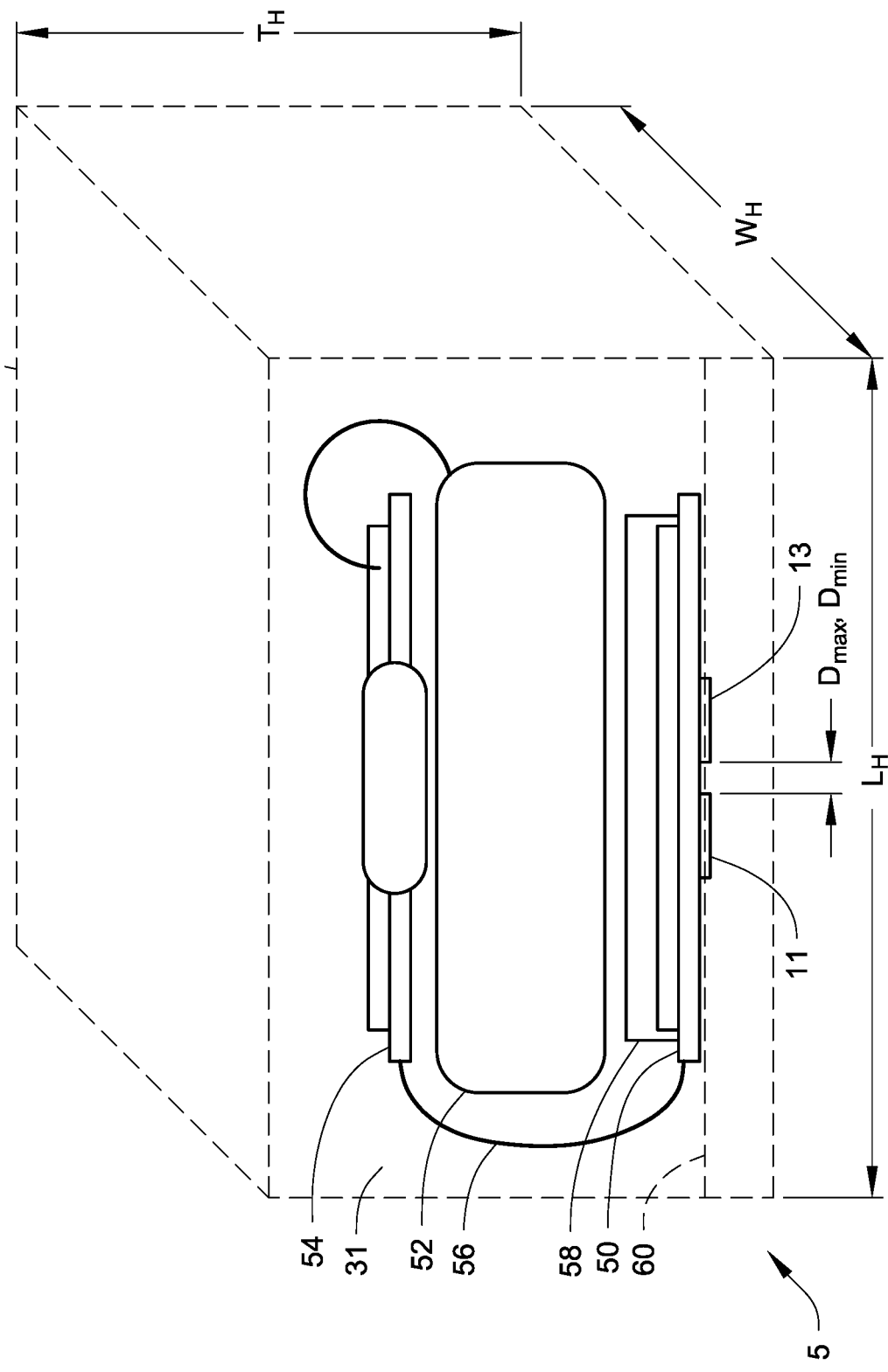
FIG. 5 is a schematic depiction of a sensor device according to an embodiment.

Referring to FIG. 5, an example configuration of the sensor device 5 is illustrated. In FIG. 5, elements that are identical or similar to elements in FIG. 1 are referenced using the same reference numerals. In FIG. 5, the antennas 11, 13 are disposed on one surface of a substrate 50 which can be, for example, a printed circuit board. At least one battery 52, such as a rechargeable battery, is provided above the substrate 50, for providing power to the sensor device 5. In addition, a digital printed circuit board 54 is provided on which the transmit circuit 15, the receive circuit 17, and the controller 19 and other electronics of the second device 5 can be disposed. The substrate 50 and the digital printed circuit board 54 are electrically connected via any suitable electrical connection, such as a flexible connector 56. An RF shield 58 may optionally be positioned between the antennas 11, 13 and the battery 52, or between the antennas 11, 13 and the digital printed circuit board 54, to shield the circuitry and electrical components from RF interference.

As depicted in FIG. 5, all of the elements of the sensor device 5, including the antennas 11, 13, the transmit circuit 15, the receive circuit 17, the controller 19, the battery 52 and the like are contained entirely within the interior space 31 of the housing 29. In an alternative embodiment, a portion of or the entirety of each antenna 11, 13 can project below a bottom wall 60 of the housing 29. In another embodiment, the bottom of each antenna 11, 13 can be level with the bottom wall 60, or they can be slightly recessed from the bottom wall 60.

The housing 29 of the sensor device 5 can have any configuration and size that one finds suitable for employing in a non-invasive sensor device. In one embodiment, the housing 29 can have a maximum length dimension $L_H$ no greater than 50 mm, a maximum width dimension $W_H$ no greater than 50 mm, and a maximum thickness dimension $T_H$ no greater than 25 mm, for a total interior volume of no greater than about 62.5 cm$^3$.

In addition, with continued reference to FIG. 5 together with FIGS. 3A-3I, there is preferably a maximum spacing $D_{max}$ and a minimum spacing $D_{min}$ between the transmit antenna 11 and the receive antenna 13. The maximum spacing $D_{max}$ may be dictated by the maximum size of the housing 29. In one embodiment, the maximum spacing $D_{max}$ can be about 50 mm. In one embodiment, the minimum spacing $D_{min}$ can be from about 1.0 mm to about 5.0 mm.

Figure 6:
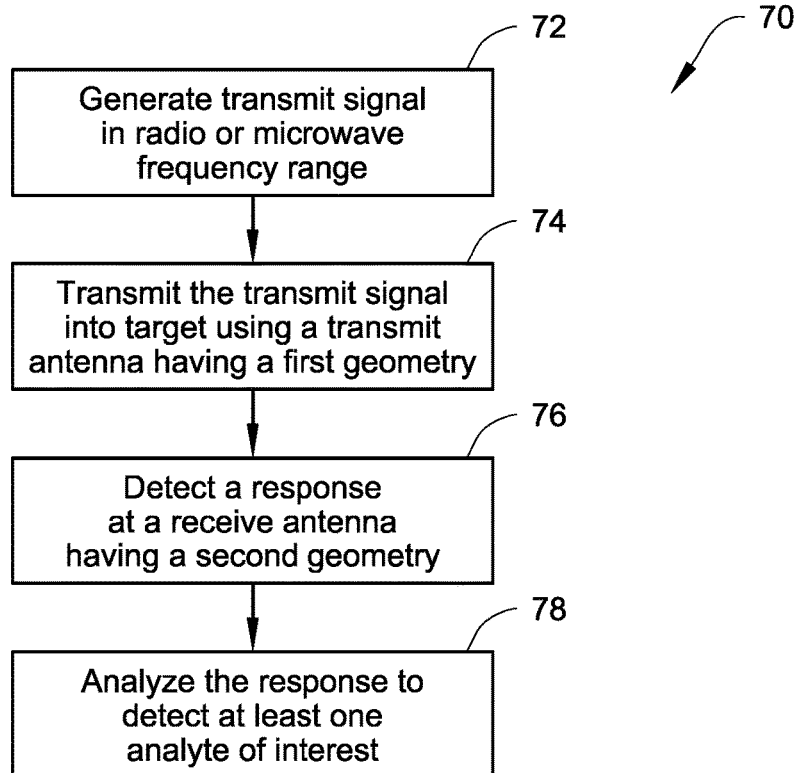
FIG. 6 is a flowchart of a method for detecting an analyte according to an embodiment.

With reference now to FIG. 6 together with FIG. 1, one embodiment of a method 70 for detecting at least one analyte in a target is depicted. The method in FIG. 6 can be practiced using any of the embodiments of the sensor device 5 described herein. In order to detect the analyte, the sensor device 5 is placed in relatively close proximity to the target. Relatively close proximity means that the sensor device 5 can be close to but not in direct physical contact with the target, or alternatively the sensor device 5 can be placed in direct, intimate physical contact with the target. The spacing between the sensor device 5 and the target 7 can be dependent upon a number of factors, such as the power of the transmitted signal. Assuming the sensor device 5 is properly positioned relative to the target 7, at box 72 the transmit signal is generated, for example by the transmit circuit 15. The transmit signal is then provided to the transmit antenna 11 which, at box 74, transmits the transmit signal toward and into the target. At box 76, a response resulting from the transmit signal contacting the analyte(s) is then detected by the receive antenna 13. The receive circuit 17 obtains the detected response from the receive antenna 13 and provides the detected response to the controller 19. At box 78, the detected response can then be analyzed to detect at least one analyte. The analysis can be performed by the controller 19 and/or by the external device 25 and/or by the remote server 27.

Figure 7:
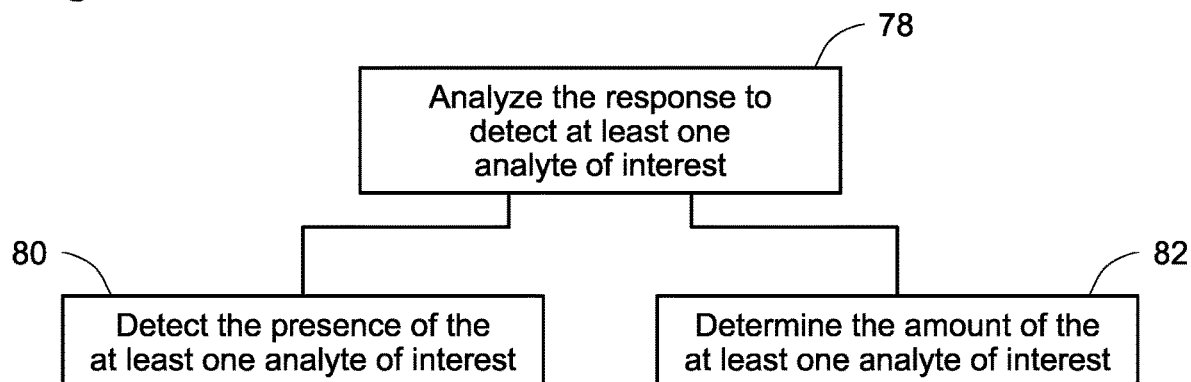
FIG. 7 is a flowchart of analysis of a response according to an embodiment.

Referring to FIG. 7, the analysis at box 78 in the method 70 can take a number of forms. In one embodiment, at box 80, the analysis can simply detect the presence of the analyte, i.e. is the analyte present in the target. Alternatively, at box 82, the analysis can determine the amount of the analyte that is present.

The interaction between the transmitted signal and the analyte may, in some cases, increase the intensity of the signal(s) that is detected by the receive antenna, and may, in other cases, decrease the intensity of the signal(s) that is detected by the receive antenna. For example, in one non-limiting embodiment, when analyzing the detected response, compounds in the target, including the analyte of interest that is being detected, can absorb some of the transmit signal, with the absorption varying based on the frequency of the transmit signal. The response signal detected by the receive antenna may include drops in intensity at frequencies where compounds in the target, such as the analyte, absorb the transmit signal. The frequencies of absorption are particular to different analytes. The response signal(s) detected by the receive antenna can be analyzed at frequencies that are associated with the analyte of interest to detect the analyte based on drops in the signal intensity corresponding to absorption by the analyte based on whether such drops in signal intensity are observed at frequencies that correspond to the absorption by the analyte of interest. A similar technique can be employed with respect to increases in the intensity of the signal(s) caused by the analyte.

Detection of the presence of the analyte can be achieved, for example, by identifying a change in the signal intensity detected by the receive antenna at a known frequency associated with the analyte. The change may be a decrease in the signal intensity or an increase in the signal intensity depending upon how the transmit signal interacts with the analyte. The known frequency associated with the analyte can be established, for example, through testing of solutions known to contain the analyte. Determination of the amount of the analyte can be achieved, for example, by identifying a magnitude of the change in the signal at the known frequency, for example using a function where the input variable is the magnitude of the change in signal and the output variable is an amount of the analyte. The determination of the amount of the analyte can further be used to determine a concentration, for example based on a known mass or volume of the target. In an embodiment, presence of the analyte and determination of the amount of analyte may both be determined, for example by first identifying the change in the detected signal to detect the presence of the analyte, and then processing the detected signal(s) to identify the magnitude of the change to determine the amount.

Figure 8:
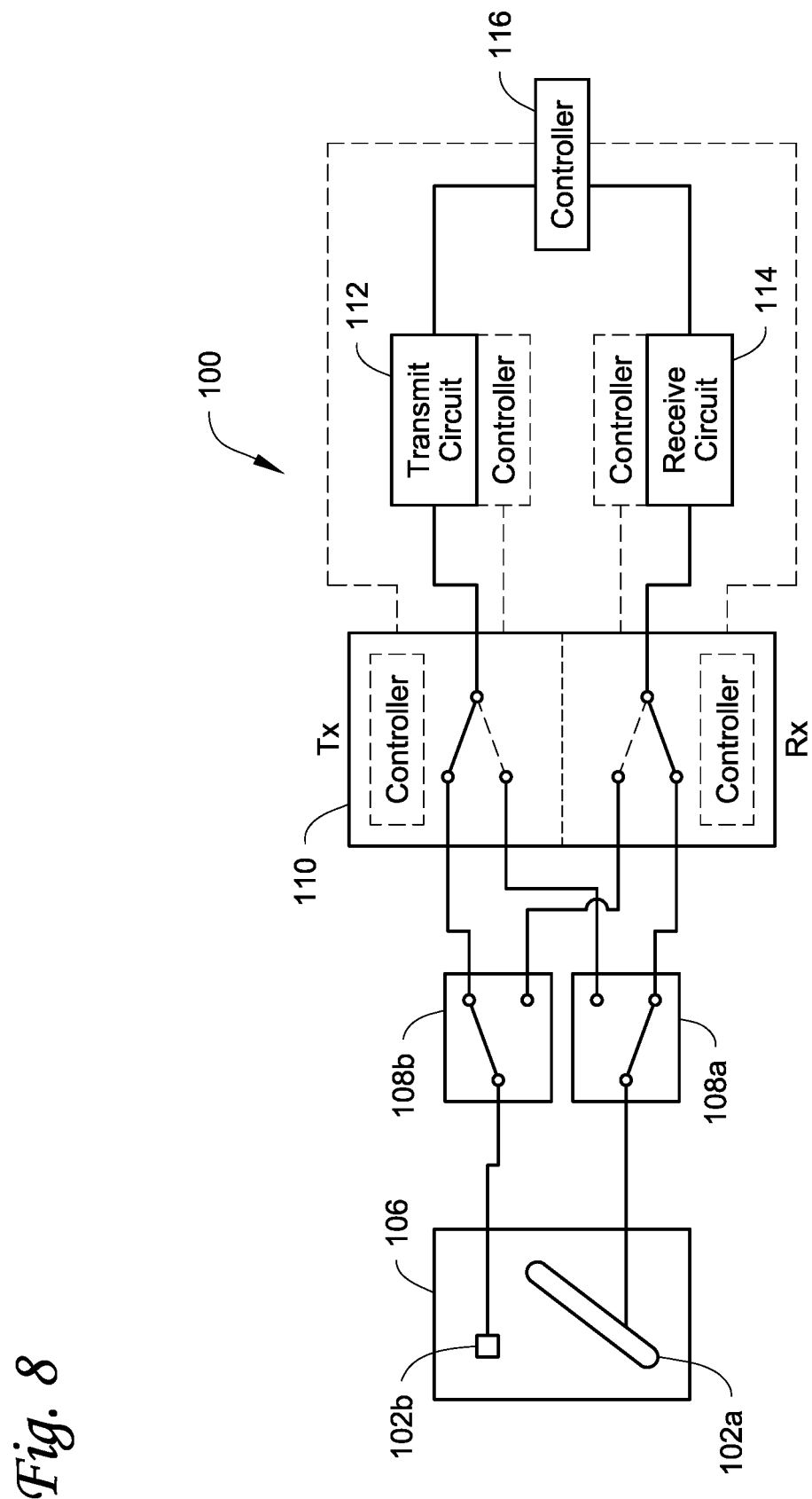
FIG. 8 is a schematic depiction of another embodiment of a non-invasive analyte sensor system with an antenna array having two antennas and configured so that either antenna can be used as a transmit antenna or as a receive antenna.
Figure 9:
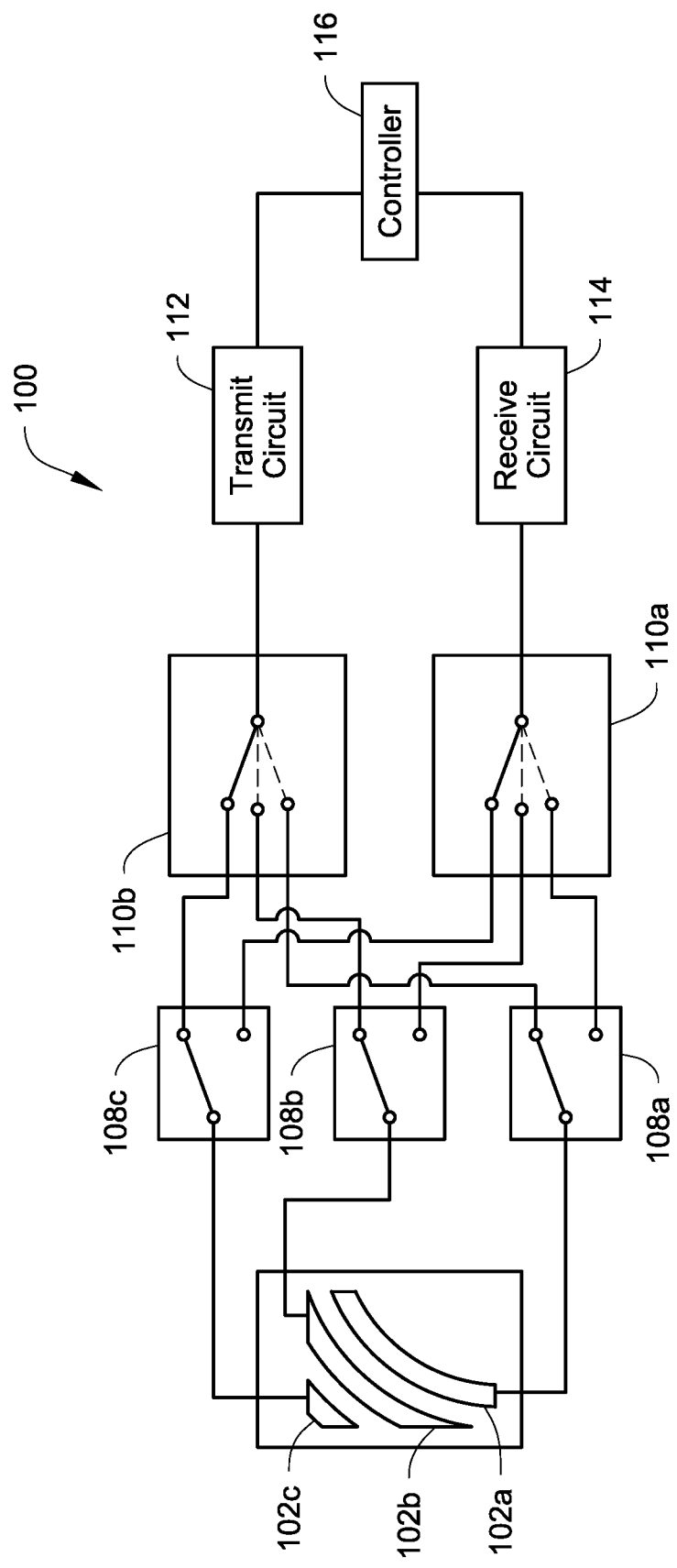
FIG. 9 is a schematic depiction of another embodiment of a non-invasive analyte sensor system with an antenna array having three antennas and configured so that either antenna can be used as a transmit antenna or as a receive antenna.
Figure 10:
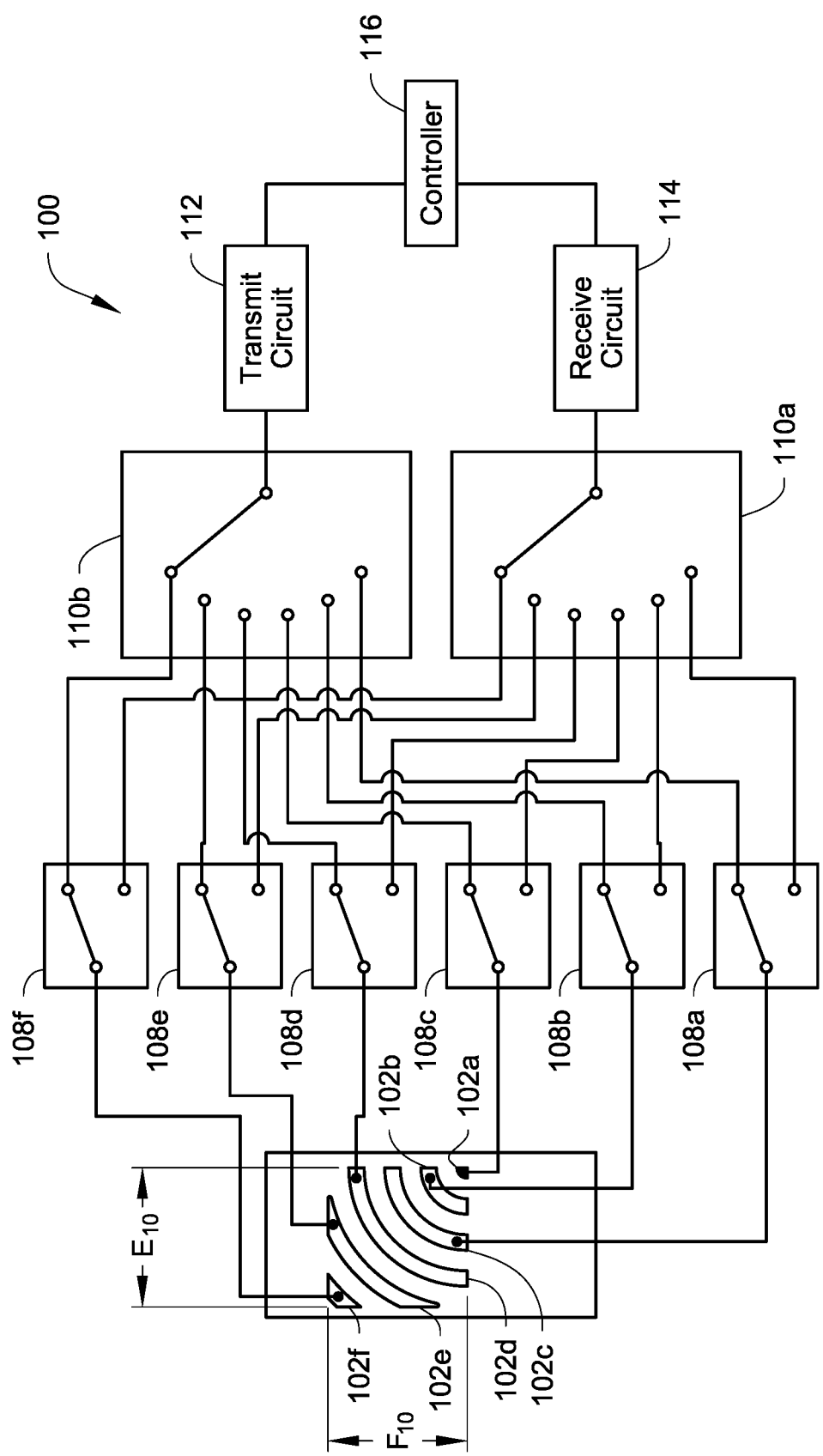
FIG. 10 is a schematic depiction of another embodiment of a non-invasive analyte sensor system with an antenna array having six antennas and configured so that either antenna can be used as a transmit antenna or as a receive antenna.

FIGS. 8-10 are schematic depictions of additional embodiments of a non-invasive analyte sensor system 100. The systems 100 depicted in FIGS. 8-10 includes at least two or more antennas, at least three or more antennas, or at least six or more antennas. However, a different number of antennas can be used. In each of the embodiments, the system 100 is configured so that one or more of the antennas of the antenna array can be used as either a transmit antenna or as a receive antenna. In FIGS. 8-10, like elements are referenced using the same reference numerals. In one embodiment, a scan routine can be implemented using the system 100 where the scan routine includes a plurality of scans, where each scan uses a different combination of the antennas to transmit a signal and detect a response. As with the previously described embodiments in FIGS. 1-7, the antenna array can be a decoupled antenna array and the antennas of the antenna array can be decoupled from one another. However, in some embodiments, the antennas of the system 100 may not be decoupled from one another. In one embodiment, the antennas used in the arrays in FIGS. 8-10 can have different geometries from each other.

In the embodiment in FIG. 8, the antenna array of the system 100 has two antennas 102a, 102b each of which can be disposed on a substrate 106 or disposed on separate substrates. The antennas 102a, 102b can have a construction similar to the construction described above with respect to FIGS. 1-7. The antennas 102a, 102b have different geometries from each other, and the antennas 102a, 102b are decoupled from each other. Switches 108a, 108b are electrically connected to each one of the antennas 102a, 102b, and one or more transmit and receive switch controllers 110 can be electrically connected each of the switches 108a, 108b. The switches 108a, 108b can have any mechanical and/or electrical construction suitable for performing the functions of the switches 108a, 108b, such as directing either one or more transmit signals to the respective antenna 102a, 102b or receiving a response detected by the other one of the antennas 102a, 102b. FIG. 8 illustrates the switches 108a, 108b as single pole, double throw switches, but other switch constructions can be used.

The switch controller(s) 110 can have any mechanical and/or electrical construction suitable for performing the functions of the switch controller 110, including controlling electrical connection of the transmit circuit 112 to any one of the antennas 102a, 102b to direct a generated transmit signal to the desired antenna 102, a, 102b to act as a transmit antenna and controlling electrical connection of the receive circuit 114 to one of the antennas 102a, 102b to act as a receive antenna. The switch controller(s) 110 can be considered to have a transmit side that is suitable for controlling the transmit function, for example by suitably controlling the positions of the either one of the switches 108a, 108b to connect to the appropriate antenna 102a, 102b and directing the transmit signal generated by a transmit circuit 112 to the appropriate antenna 102a, 102b. The switch controller(s) 110 can also be considered to have a receive side that is suitable for controlling the receive function, for example by suitably controlling the positions of the either one of the switches 108a, 108b to connect to the appropriate antenna 102a, 102b for receiving the response and directing the response to a receive circuit 114. The switch controller(s) 110 can have one or more controllers integrated therewith or suitably connected thereto for managing and controlling the control functions of the switch controller(s) 110.

Control of the switch controller(s) 110 may alternatively be achieved using one or more other controllers of the system 100, for example a controller associated with the transmit circuit 112, a controller associated with the receive circuit 114, a main controller 116 of the system 100, or one or more other controllers.

The transmit circuit 112 and the receive circuit 114 are each electrically connected to the switch controller 110. The transmit circuit 112 is similar in function to the transmit circuit 15 described above in that the transmit circuit 112 is configured to generate at least one transmit signal in the radio or microwave frequency range of the electromagnetic spectrum, for example about10 kHz to about 100 GHz, to be transmitted into the target containing the at least one analyte of interest by whichever one of the antennas 102a, 102b is acting as the transmit circuit as determined by the switch controller 110. In addition, the receive circuit 114 is similar in function to the receive circuit 17 described above in that the receive circuit 114 is configured to receive a response detected by whichever one of the antennas 102a, 102b is acting as the receive antenna, where the response results from transmission of the at least one transmit signal into the target. The main controller 116 is connected to the transmit circuit 112 to control generation of the transmit signal(s) by the transmit circuit 112. The controller 116 (or a separate controller) is also connected to the receive circuit 114 and is similar in function to the controller 19 described above, for example to store the response(s) detected by the receive antenna in suitable storage/memory and/or to analyze the response(s).

In FIG. 8, one or more of the elements 108a, 108b, 110, 112, 114 and 116 can be combined together functionally and/or mechanically rather than being separate elements. In addition, the transmit and receive switch controller 110 can be physically separated into a transmit switch controller that is separate from a receive switch controller as described below with respect to FIGS. 9 and 10. In addition, communications between one or more of the elements 108a, 108b, 110, 112, 114 and 116 can be achieved via wired connections and/or via wireless connections. Further, the operational positions of the switches 108a, 108b and the switch controller(s) 110 can be controlled using any suitable means, for example software and/or hardware, to ensure that at any moment in time, the switch controller(s) 110 is not connected to the same switch 108a, 108b at the same time. Moreover, when implementing a scan routine as described below, suitable techniques, such as the use of time stamps, can be used to differentiate between and/or identify the results of each scan, as well as indicate the frequency(ies) at which each scan was conducted.

The construction in FIG. 8 is such that a scan routine can be implemented where the scan routine includes a plurality of scans. In one scan of the scan routine, the antenna 102a can be used as the transmit antenna while the antenna 102b is used as the receive antenna. In another scan, the antenna 102b can be used as the transmit antenna while the antenna 102a is used as the receive antenna. The results of the two scans can then be analyzed to determine the analyte, for example as described above, and optionally determine the amount of the analyte that is present.

FIG. 9 illustrates another embodiment of the system 100 that functions similarly to the system 100 in FIG. 8. In the embodiment in FIG. 9, the antenna array of the system 100 has three antennas 102a, 102b, 102c each of which is disposed on the substrate 106. The system further includes three of the switches 108a, 108b, 108c, a receive switch controller 110a, and a transmit switch controller 110b separate from the receive switch controller 110a.

In the embodiment in FIG. 9, the number of scans of the scan routine is greater than in FIG. 8. The following table (Table 1) lists a portion of a scan routine showing some of the scans using different antenna combinations that can be implemented. The scan routine can include a larger or smaller number of scans, and other scans using different antenna combinations can be implemented. The results of the scans can then be analyzed to determine the analyte, for example as described above, and optionally determine the amount of the analyte that is present.

TABLE 1

| Scan # | Tx antenna | Rx antenna |
|---|---|---|
| 1 | 102a | 102b |
| 2 | 102a | 102c |
| 3 | 102b | 102a |
| 4 | 102b | 102c |
| 5 | 102c | 102a |
| 6 | 102c | 102b |
| 7 | 102a + 102b | 102c |

TABLE 1-continued

| Scan # | Tx antenna | Rx antenna |
|---|---|---|
| 8 | 102a | 102b + 102c |
| 9 | 102b + 102c | 102a |
| Etc. | Etc. | Etc. |

As indicated in Table 1, a single scan can use one antenna as a transmit antenna and one antenna as a receive antenna, or use two antennas as transmit antennas and one antenna as a receive antenna, or use one antenna as a transmit antenna and two antennas as receive antennas. In some embodiments, it is also possible that in a single scan, an antenna could be used as both a transmit antenna and as a receive antenna.

FIG. 10 illustrates still another embodiment of the system 100 that functions similarly to the systems 100 in FIGS. 8 and 9. In the embodiment in FIG. 10, the antenna array of the system 100 has six antennas 102a-f each of which is disposed on the substrate 106, and six of the switches 108a-f. In one embodiment, the antenna array formed by the six antennas 102a-f can have dimensions $E_{10} \times F_{10}$ which does not exceed 30.0 mm by 30.0 mm. Due to the larger number of antennas in FIG. 10 compared with FIGS. 8 and 9, the system 100 in FIG. 10 permits implementation of scan routines using a larger number of scans using a larger number of antenna combinations. Table 2 below lists a portion of a scan routine showing some of the scans using different antenna combinations that can be implemented. The scan routine can include a larger or smaller number of scans, and other scans using different antenna combinations can be implemented. The results of the scans can then be analyzed to determine the analyte, for example as described above, and optionally determine the amount of the analyte that is present.

TABLE 2

| Scan # | Tx antenna | Rx antenna |
|---|---|---|
| 1 | 102a | 102b |
| 2 | 102b | 102c |
| 3 | 102b | 102d |
| 4 | 102c | 102f |
| 5 | 102e | 102a |
| 6 | 102f | 102b |
| 7 | 102a + 102b | 102c |
| 8 | 102a + 102b | 102c + 102d |
| 9 | 102a + 102c | 102f |
| 10 | 102a + 102c | 102b + 102d |
| 11 | 102b | 102a + 102f |
| Etc. | Etc. | Etc. |

As indicated in Table 2, a single scan can use one antenna as a transmit antenna and one antenna as a receive antenna, use two or more antennas as transmit antennas and one antenna as a receive antenna, use one antenna as a transmit antenna and two or more antennas as receive antennas, use two or more antennas as transmit antennas and two or more antennas as receive antennas, etc. In some embodiments, it is also possible that in a single scan, an antenna could be used as both a transmit antenna and as a receive antenna.

The systems 100 of FIGS. 8-10 can be used for non-invasive detection of an analyte. For example, in the systems 100, in the antenna array having the at least two antennas, the transmit circuit 112 can be selectively connected to any one or more of the at least two antennas of the antenna array, for example using the switch controller 110, 110a. At least one transmit signal is generated using the transmit circuit 112, where the at least one transmit signal has at least two different frequencies each of which is in a radio or microwave frequency range of the electromagnetic spectrum. The at least one transmit signal is transmitted into a target containing at least one analyte of interest using the one or more of the at least two antennas connected to the transmit circuit 112. In addition, the receive circuit 114 is selectively connected to a different one or more of the at least two antennas of the antenna array. The receive circuit and the different one or more of the at least two antennas of the antenna array are then used to detect a response resulting from transmission of the at least one transmit signal into the target containing the at least one analyte of interest.

In operation of either one of the systems 100 of FIGS. 8-10, a scan routine can implemented using the antenna array. In a first scan, a first combination of two or more of the antennas is used to transmit a first transmit signal that is in a radio or microwave frequency range of the electromagnetic spectrum into a target containing at least one analyte of interest and used to detect a response resulting from transmission of the first transmit signal into the target containing the at least one analyte of interest. In a second scan, a second combination of two or more of the antennas, different from the first combination, is used to transmit a second transmit signal that is in a radio or microwave frequency range of the electromagnetic spectrum into the target containing the at least one analyte of interest and used to detect a response resulting from transmission of the second transmit signal into the target containing the at least one analyte of interest. Depending upon the number of antennas in the array, the scan routine can include additional scans using additional combinations of two or more of the antennas to transmit the transmit signal and to detect a response.

The scan routine can be implemented at a number of discrete frequencies over a range of frequencies as described in WO 2019/217461, the entire contents of which are incorporated herein by reference. In the scan routine, for each scan at each frequency, a transmit signal can be transmitted by whichever antenna(s) is functioning as the transmit antenna and a response is detected a plurality of times, for example 20 times, at the antenna(s) that is functioning as the receive antenna. The detected responses can then be averaged to obtain the $S_{21}$ value.

Figure 11:
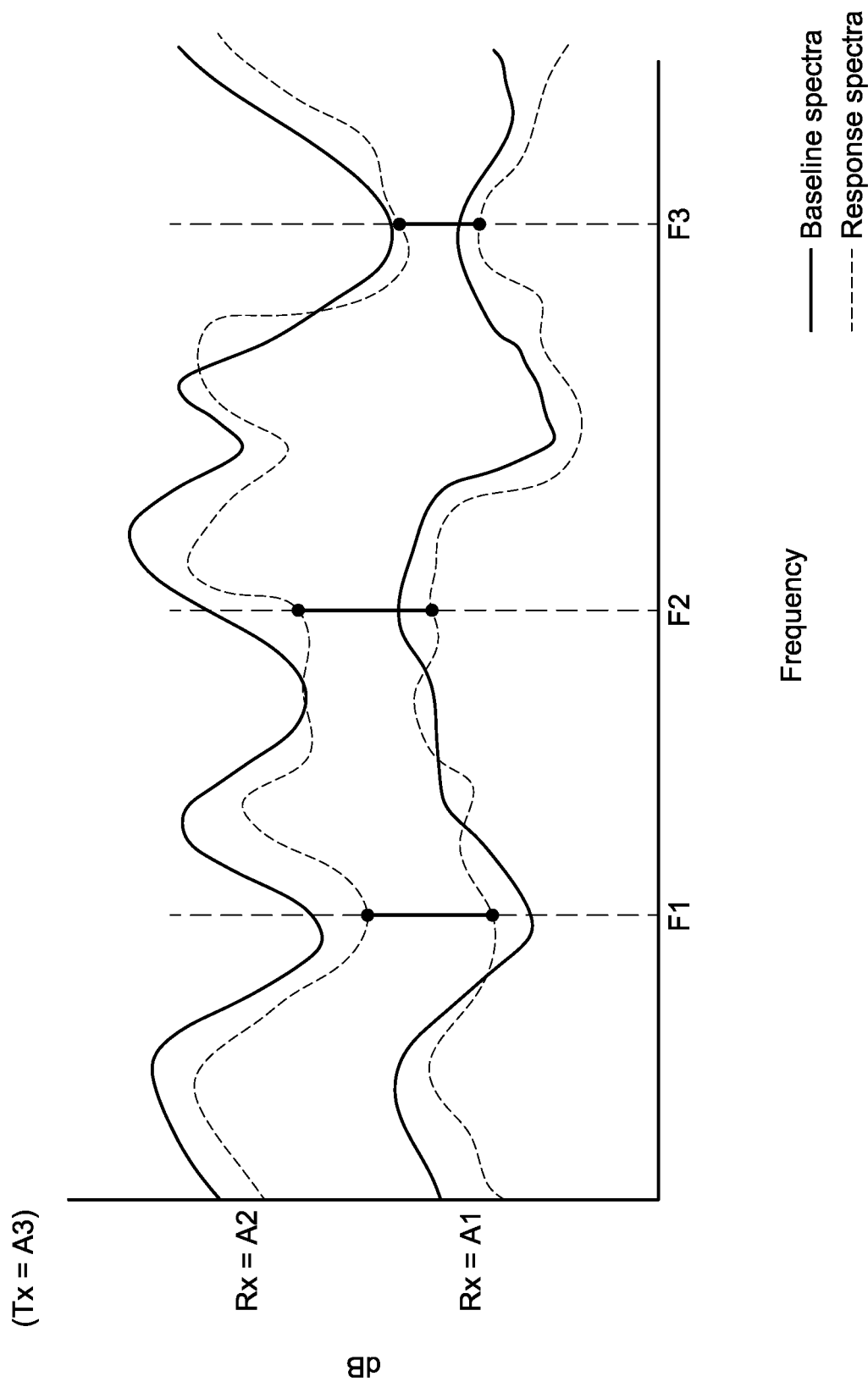
FIG. 11 depicts an example of results from a scan routine.

The analyte can be detected as described above. In one embodiment, a min/max subtraction method can be used at selected frequencies across the various scans of the scan routine. In another embodiment, a difference between power received by the antenna(s) acting as the receive antenna(s) at selected frequencies can be used. For example, FIG. 11 illustrates an example where an antenna (A3) is used as the transmit antenna Tx and antennas (A1 and A2) are used as receive antennas Rx. A baseline response spectra over a frequency range of interest is illustrated, and a response spectra detected by the antennas (A1, A2) is also depicted. A change in spectra between the baseline response spectra and the detected response spectra is different between the receive antennas (A1, A2). At particular frequencies F1, F2, F3, etc., a signal (represented by the vertical bar indicating the difference between the two dB values of the detected response spectra) correlating to analyte concentration can be calculated.

As indicated above, the data obtained by the sensor 5 needs to be analyzed. The analysis can occur on the sensor 5 or on one or more devices or systems separate from the sensor 5. Unless otherwise indicated by the Applicant, the term devices or systems is intended to be construed broadly as encompassing any type of devices or systems that can analyze the data obtained by the sensor 5. Examples of devices or system that can be used to analyze the data include, but are not limited to, hardware-based computing devices or systems; cloud-based computing devices or systems; machine learning devices or systems including active learning devices or systems; artificial intelligence-based devices or systems; neural network-based devices or systems; combinations thereof; and any other types of devices and systems that are suitable for analyzing the data.

One or more output signals resulting from or based on the analysis are then generated. In some embodiments, the output signal(s) is generated by the device(s) or system(s) that analyze the data. The output signal(s) is directed to one or more other devices or systems that implement an action based on the output signal(s). In one embodiment, the output signal(s) is directed to one or more notification devices (discussed further below) which generates at least one human perceptible notification for example to provide a perceptible signal or alert to the patient and/or a caregiver of the patient. In this embodiment, the output signal(s) may be referred to as a notification signal(s). In another embodiment, the output signal(s) may be directed to one or more other machine(s) or system(s), for example a medical device such as an insulin pump, that modifies the operation of the other machine(s) or system(s). In one embodiment, the output signal(s) or separate output signals can be directed to both one or more notification devices and one or more other machine(s) or system(s). In one embodiment, the output signal(s) can be stored in a suitable data storage separately from, or in addition to, being sent to one or more notification devices and/or to one or more other devices or systems.

Figure 12:
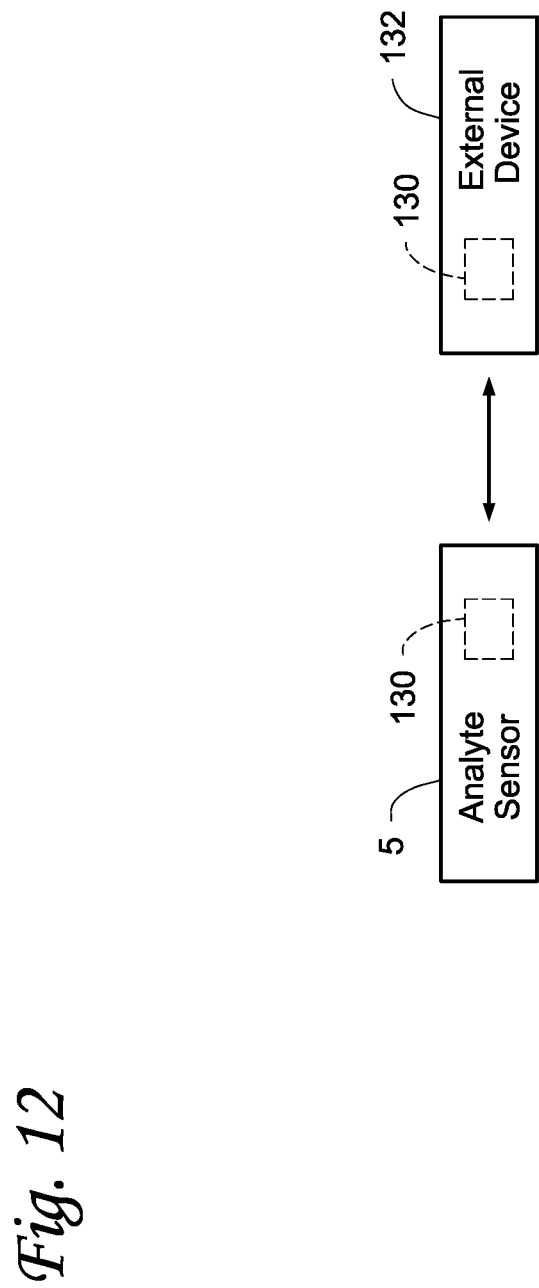
FIG. 12 depicts a system that includes the analyte sensor and an external device in communication with the analyte sensor, with the system including a notification device.
Figure 14:
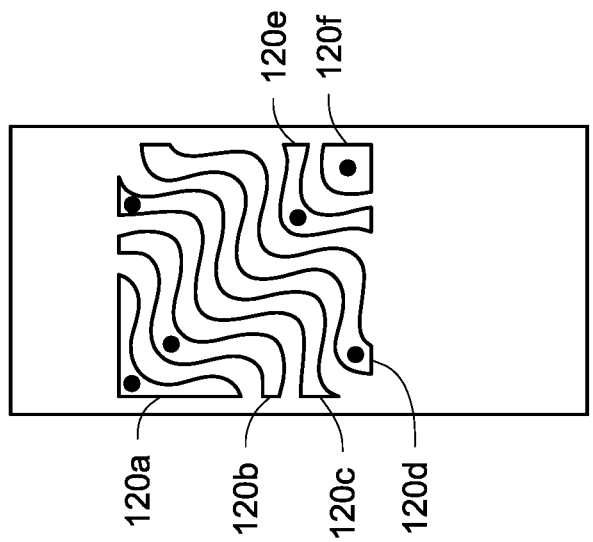
FIGS. 13-19 are top views of additional examples of antenna arrays and antenna configurations that can be used in the embodiments described herein.
Figure 13:
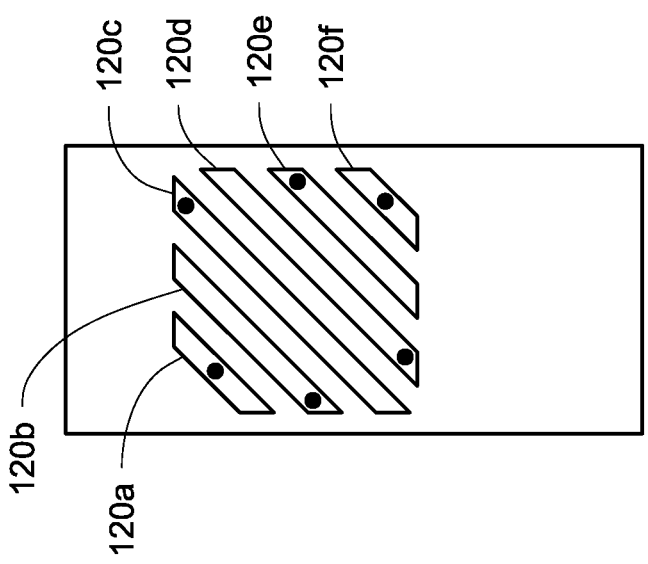
Figure 16:
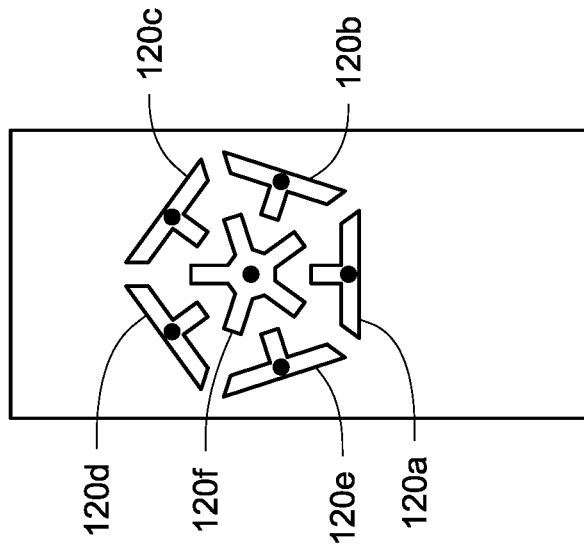
Figure 15:
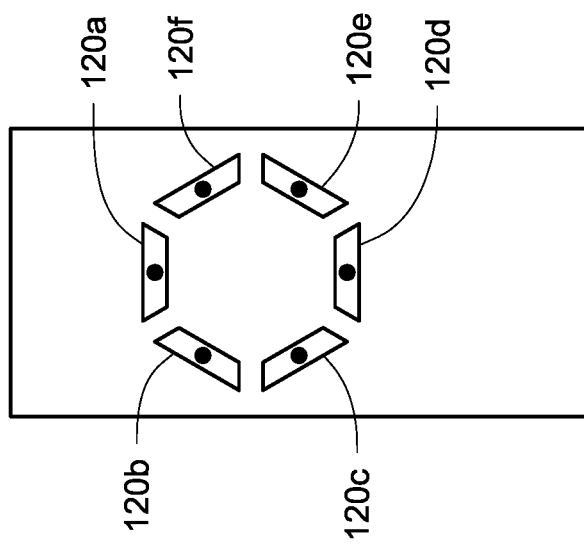

FIG. 12 illustrates one non-limiting example of an output signal generation. In this example, an output signal is sent to a notification device 130 included in the system 100 to generate at least one human perceptible notification resulting from the analysis. The notification device 130 can be connected, directly or indirectly, to the system 100. For example, in one embodiment, the notification device 130 can be incorporated on the sensor 5 to provide the at least one human perceptible notification directly to the person using or wearing the device 5. In another embodiment, the notification device 130 can be incorporated into a device 132 that is physically separate from the device 5 including, but not limited to, a mobile phone (a.k.a. cell phone, smartphone); a tablet computer; a laptop computer; a personal computer; a wearable device such as a watch or a head-mounted device or clothing; a video game console; furniture such as a chair; a vehicle such as a car, automobile or truck; lightbulbs; smart home appliances such as a smart refrigerator; and a use specific device similar to these devices that is specifically designed to function with the sensor 5. The at least one human perceptible notification generated by the notification device 130 can be one or more of an audible sound notification, a visual notification, a haptic notification, or an olfactory notification. Operation of the notification device 130 can be triggered by a notification or output signal that is generated resulting from the analysis. The notification signal can be generated by the device 5, for example by the main controller thereof, or by a separate device or system as described above that performs the analysis after receiving the data from the device 5.

In each of the embodiments in FIGS. 8-10, the systems 100 can be used like in the embodiments in FIGS. 1 and 5, where the system includes the sensor housing 29, the antenna array is attached to the sensor housing, the transmit circuit 112 is disposed in the sensor housing, the receive circuit 114 is disposed in the sensor housing, and the battery 52 disposed in the sensor housing provides electrical power to the components including the switch controller 110, 110a, 110b, the transmit circuit 112, the receive circuit 114, and the controller 116.

FIGS. 13-19 are top views of additional examples of antenna arrays and antenna configurations and shapes that can be used in any of the embodiments described herein including the system 100 in FIG. 10. In each of the embodiments in FIGS. 13-19, the antennas of each array have different geometries from one another and the antennas are decoupled from one another.

The embodiments in FIGS. 13-16 each depicts a decoupled antenna array with six antennas 120a-f. However, each antenna array can use a smaller or larger number of antennas. In testing conducted to date, the Applicant has determined that the antenna array depicted in FIG. 10 and the antenna depicted in FIG. 13 achieve the best results when compared to the antenna arrays in FIGS. 14-16.

Figure 17:
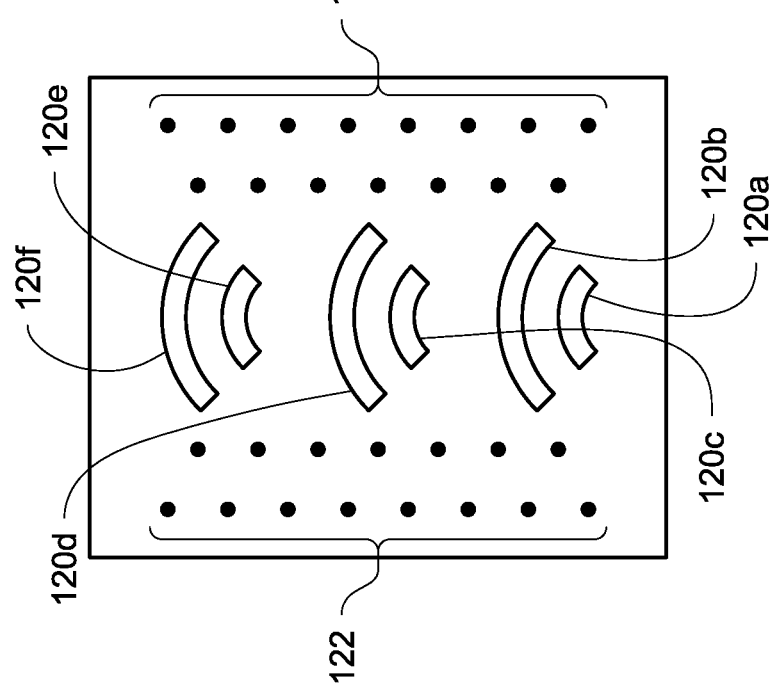

FIG. 17 depicts another embodiment of a decoupled antenna array with six primary or larger antennas 120a-f, as well as a number of smaller point antennas 122 disposed to each side of the larger antennas 120a-f. The use of the point antennas 122 increase the number of antennas that can be located in the array, thereby increasing the number of scans and antenna combinations that can be utilized in a scan routine using the antenna array in FIG. 17.

Figure 18:
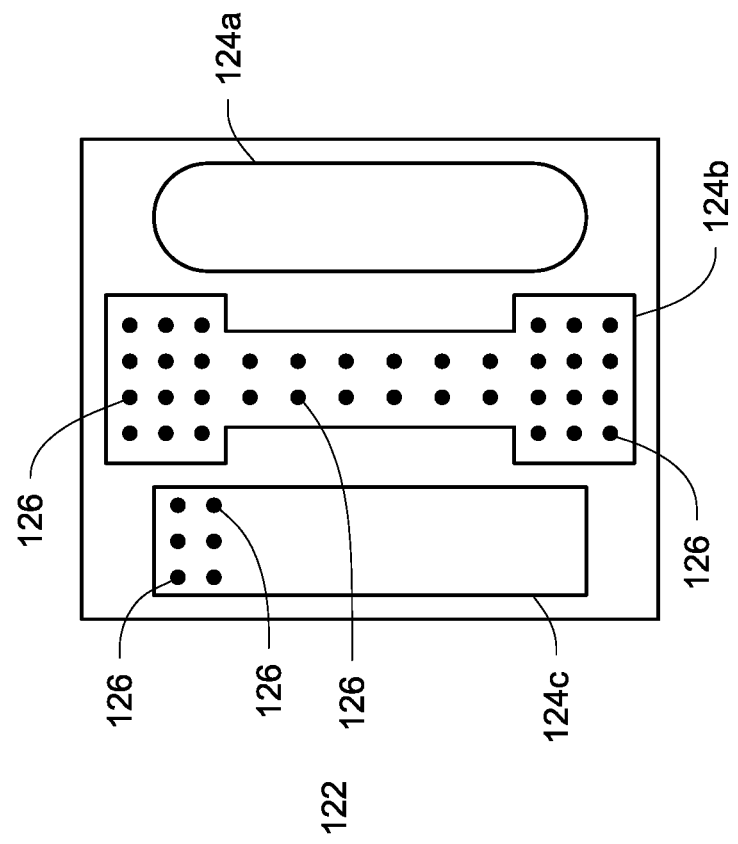

FIG. 18 depicts another embodiment of a decoupled antenna array with three antennas 124a-c. One or more of the antennas 124a-c is formed with holes 126 therein which helps to change the geometry of the antennas 124a-c.

Figure 19:
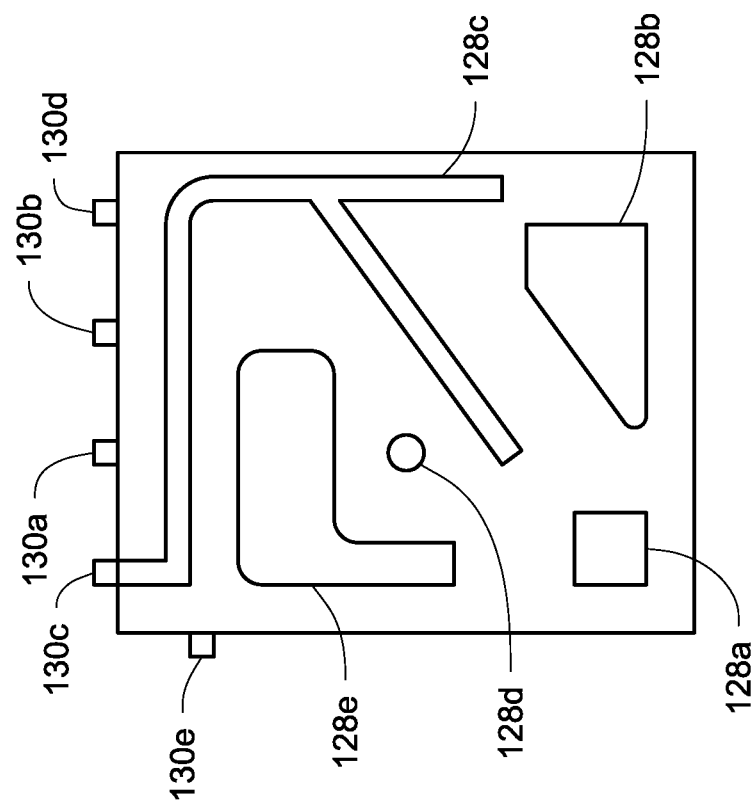

FIG. 19 depicts another embodiment of a decoupled antenna array with five antennas 128a-e and antenna ports 130a-e for connecting to each antenna 128a-e.

Figure 20:
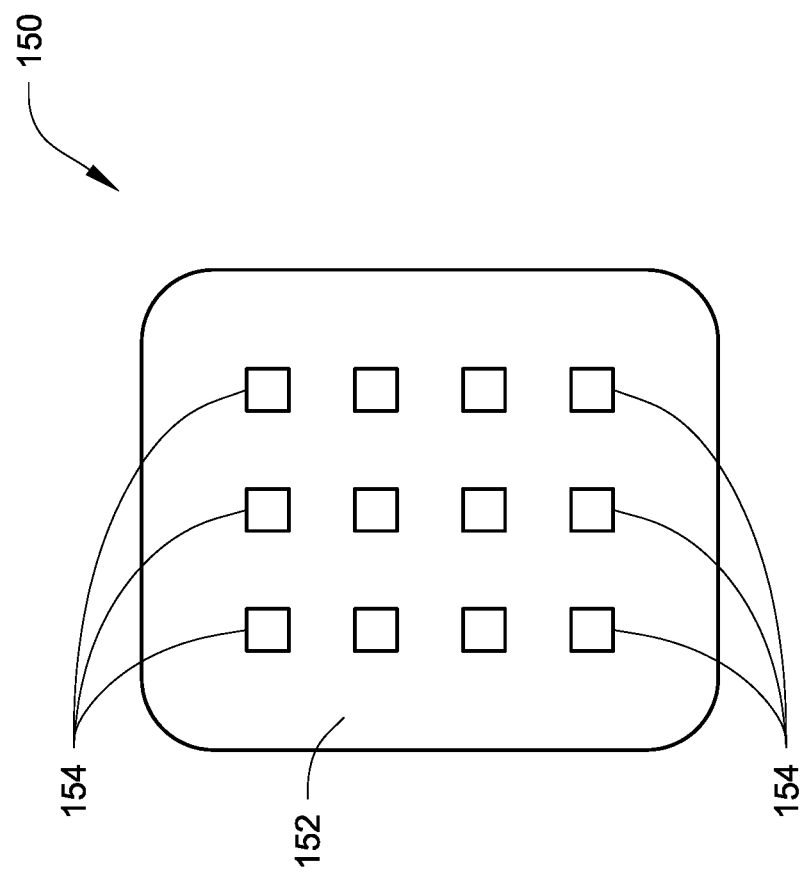
FIG. 20 is a schematic depiction of a portion of another embodiment of a non-invasive analyte sensor system with a non-invasive analyte sensor that uses electromagnetic energy in the form of light to perform non-invasive analyte sensing described herein.

FIGS. 20, 21A and 21B schematically depict another example of a non-invasive analyte sensor 150 that forms a portion of another embodiment of a non-invasive analyte sensor system. The non-invasive analyte sensor 150 uses electromagnetic energy in the form of light waves at selected electromagnetic frequencies to perform non-invasive analyte sensing described herein. The sensor 150 includes a housing 152 and a sensor array that includes a plurality of detector elements 154 each of which can emit electromagnetic energy in the form of light as well as act as a light detector (or photodetector). The illustrated example depicts the array as having a total of twelve of the detector elements 154 arranged into a 3×4 or 4×3 array. However, a larger or smaller number of the detector elements 154 can be provided in the array. In addition, the array can have other arrangements including being disposed in a circular array. The emitted light penetrates the target and reflects from an analyte, with at least one detector element detecting the reflected light.

Referring to FIGS. 21A and 21B, some or all the detector elements 154 may be flush with a surface 156 of the housing 152 so that light emitted by each detector element 154 may be transmitted from the sensor 150 and each detector element 154 may detect returning light. In another embodiment, some or all of the detector elements 154 may be recessed within the housing 152 but the light from each detector element 154 is suitably channeled to the outside and returning light suitably channeled to the detector elements 154. In still another embodiment, some or all of the detector elements 154 may project (partially or completely) from the housing 152.

The detector elements 154 are controlled in a manner whereby any one or more of the detector elements 154 can emit light and any one or more of the detector elements 154 can act as a light detector. In one embodiment, the detector elements 154 may be light emitting diodes (LEDs) and the array that includes the LEDs can be referred to as an LED array. LEDs that can be selectively controlled to emit light (i.e. a photoemitter) or detect light (i.e. a photodetector) are known. See Stojanovic et al., An optical sensing approach based on light emitting diodes, Journal of Physics: Conference Series 76 (2007); Rossiter et al., A novel tactile sensor using a matrix of LEDs operating in both photoemitter and photodetector modes, Proc of 4th IEEE International Conference on Sensors (IEEE Sensors 2005). See also U.S. Pat. No. 4,202,000 the entire contents of which are incorporated herein by reference.

The LEDs that are used preferably permit at least two different wavelengths of light to be emitted (in other words, one LED emits light having a first wavelength and a second LED emits light having a second wavelength different than the first wavelength). In another embodiment, at least three or more different wavelengths of light can be emitted by the various LEDs. In one embodiment, each one of the LEDs can emit a different wavelength of light. In one embodiment, two or more of the LEDs can emit the same wavelength of light. The LED's can emit wavelengths that are in the human visible spectrum (i.e. about 380 nm to about 760 nm) including, but not limited to, wavelengths that are visibly perceived as blue light, red light, green light, white light, orange light, yellow light, and other colors, as well as emit wavelengths that are not in the human visible spectrum including, but not limited to, infrared wavelengths and ultraviolet wavelengths. Combinations of wavelengths in the visible and non-visible spectrums may also be used. The light waves emitted by the sensor 150 function in a manner similar to the RF waves emitted by the sensors in FIGS. 1-19 since both are electromagnetic waves. For example, referring to FIG. 21A, the light waves 158 penetrate into a target and reflect from an analyte in the target to form the returning light waves 160 which are detected.

The detector elements 154 can be controlled using a control system similar to the control system depicted in FIGS. 8-10 including the switches, switch controllers, transmit circuit, receive circuit, and controller described in FIGS. 8-10. For example, FIG. 21A depicts an example where the detector element 154a on the left is controlled to function as a photoemitter emitting light waves 158 and the detector element 154b on the right is controlled to function as a photodetector that detects returning light waves 160 resulting from the transmission of the light waves 158. FIG. 21B depicts an example where the detector element 154b on the right is controlled to function as a photoemitter emitting light waves 162 and the detector element 154c in the center is controlled to function as a photodetector that detects returning light waves 164 resulting from the transmission of the light waves 162.

A scan routine can be implemented with the sensor 150 at a number of discrete electromagnetic frequencies over a range of electromagnetic frequencies based on the different wavelengths of the LEDs. A response spectra is detected by each of the detector element(s) 154 functioning as the photodetector with the response spectra being correlated to a particular analyte and analyte concentration.

In another embodiment, a non-invasive sensor can include both two or more antennas as described herein as well as two or more of the LEDs described herein. The antennas and the LEDs can be used together to detect an analyte. In another embodiment, the antennas can be used to perform a primary detection while the LEDs can confirm the primary detection by the antennas. In another embodiment, the LEDs can be used to perform a primary detection while the antennas can be used to confirm the primary detection by the LEDs.

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A method of detection of an analyte, comprising:
    in a detector array having at least three detector elements that are configured to emit and receive electromagnetic waves, selectively connecting a transmit circuit to any one or more of the at least three detector elements of the detector array using an array of switches connected between the at least three detector elements and the transmit circuit, each detector element is associated with a corresponding one of the switches in the array of switches;
    generating at least one transmit signal using the transmit circuit, the at least one transmit signal is in a radio or microwave frequency or visible range of the electromagnetic spectrum;
    transmitting the at least one transmit signal into a target containing at least one analyte of interest using the one or more of the at least three detector elements connected to the transmit circuit;
    selectively connecting a receive circuit to a different one or more of the at least three detector elements of the detector array using the array of switches connected between the at least three detector elements and the receive circuit;
    using the receive circuit and the different one or more of the at least three detector elements of the detector array to detect a response resulting from transmission of the at least one transmit signal into the target containing the at least one analyte of interest.

2. The method of claim 1, wherein selectively connecting the transmit circuit to any one or more of the at least three detector elements of the detector array and/or selectively connecting the receive circuit to the different one or more of the at least three detector elements of the detector array occur before, during, or after generating the at least one transmit signal using the transmit circuit.

3. The method of claim 1, further comprising analyzing the response to detect the at least one analyte of interest.

4. The method of claim 3, wherein detecting the at least one analyte of interest comprises determining an amount of the at least one analyte of interest.

5. The method of claim 3, further comprising using results of the analysis to generate an output signal, and using the output signal to modify operation of a device or system.

6. The method of claim 1, wherein the at least one analyte of interest comprises blood glucose, blood alcohol, white blood cells, or luteinizing hormone.

7. The method of claim 1, wherein the at least three detector elements comprise at least three antennas, and the at least one transmit signal is in a radio or microwave frequency range of the electromagnetic spectrum.

8. The method of claim 7, wherein the at least three antennas are decoupled from one another.

9. The method of claim 7, wherein the at least three antennas have geometries that differ from one another.

10. The method of claim 7, wherein the detector array has at least six antennas, and the detector array does not exceed 30.0 mm by 30.0 mm.

11. The method of claim 7, wherein the radio or microwave frequency range is between about 10 kHz to about 100 GHz.

12. The method of claim 1, wherein the at least three detector elements comprise at least three light emitting diodes, and the at least one transmit signal is in a visible range of the electromagnetic spectrum.

13. The method of claim 12, wherein the at least three light emitting diodes emit different wavelengths of light.

14. The method of claim 1, wherein the target is human tissue, animal tissue, plant tissue, an inanimate object, soil, a fluid, genetic material, or a microbe.

15. The method of claim 1, further comprising one of the following:
    a transmit switch controller connected between the transmit circuit and the array of switches, and a receive switch controller connected between the receive circuit and the array of switches; or
    a switch controller connected between the transmit circuit and the array of switches and connected between the receive circuit and the array of switches.

16. A method of non-invasive detection of an analyte, comprising:
    in a detector array having at least three decoupled elements each of which is configured to act as an antenna and where the at least three decoupled elements have geometries that differ from one another, selectively connecting a transmit circuit to any one or more element of the at least three decoupled elements of the detector array using an array of switches connected between the at least three decoupled elements and the transmit circuit, each decoupled element is associated with a corresponding one of the switches in the array of switches;
    generating at least one transmit signal using the transmit circuit, the at least transmit signal having at least two different frequencies each of which falls within a range of between about 10 kHz to about 100 GHz;
    transmitting the at least one transmit signal into a target containing at least one analyte of interest using the any one or more element of the at least three decoupled elements connected to the transmit circuit;
    selectively connecting a receive circuit to one or more different elements of the at least three decoupled elements of the detector array using the array of switches connected between the at least three decoupled elements and the receive circuit; and
    using the receive circuit and the one or more different elements of the at least three decoupled elements of the detector array to detect a response resulting from transmission of the at least one transmit signal into the target containing the at least one analyte of interest.

17. The method of claim 16, wherein selectively connecting the transmit circuit to the any one or more element of the at least three decoupled elements of the detector array and selectively connecting the receive circuit to the one or more different elements of the at least three decoupled elements of the detector array occur before, during, or after generating the at least one transmit signal using the transmit circuit.

18. The method of claim 16, further comprising analyzing the response to detect the at least one analyte of interest.

19. The method of claim 18, wherein detecting the at least one analyte of interest comprises determining an amount of the at least one analyte of interest.

20. The method of claim 18, further comprising using results of the analysis to generate an output signal, and using the output signal to modify operation of a device or system.

21. The method of claim 16, wherein the at least one analyte of interest comprises blood glucose, blood alcohol, white blood cells, or luteinizing hormone.

22. The method of claim 16, wherein the detector array has at least six of the decoupled elements, and the detector array does not exceed 30.0 mm by 30.0 mm.

23. The method of claim 16, wherein the target is human tissue, animal tissue, plant tissue, an inanimate object, soil, a fluid, genetic material, or a microbe.

24. The method of claim 16, further comprising one of the following:
- a transmit switch controller connected between the transmit circuit and the array of switches, and a receive switch controller connected between the receive circuit and the array of switches; or
- a switch controller connected between the transmit circuit and the array of switches and connected between the receive circuit and the array of switches.

\* \* \* \* \*